United States Patent
Chandrasekher et al.

(10) Patent No.: US 7,704,950 B2
(45) Date of Patent: Apr. 27, 2010

(54) METHODS OF USING SOLUBLE HETERODIMERIC CYTOKINE RECEPTOR

(75) Inventors: Yasmin A. Chandrasekher, Saratoga, CA (US); Julia E. Novak, Suquamish, WA (US); Donald C. Foster, Lake Forest Park, WA (US); Wenfeng Xu, Seattle, WA (US); Stephen R. Jaspers, Edmonds, WA (US)

(73) Assignee: ZymoGenetics, Inc., Seattle, WA (US)

(*) Notice: Subject to any disclaimer, the term of this patent is extended or adjusted under 35 U.S.C. 154(b) by 0 days.

(21) Appl. No.: 11/690,915

(22) Filed: Mar. 26, 2007

(65) Prior Publication Data

US 2007/0173451 A1    Jul. 26, 2007

Related U.S. Application Data

(63) Continuation of application No. 10/471,151, filed as application No. PCT/US02/07214 on Mar. 7, 2002, now abandoned.

(60) Provisional application No. 60/274,560, filed on Mar. 9, 2001, provisional application No. 60/299,865, filed on Jun. 21, 2001.

(51) Int. Cl.
   *A61K 38/00* (2006.01)
   *A61K 45/00* (2006.01)
(52) U.S. Cl. .................... 514/12; 424/85.1; 424/85.2
(58) Field of Classification Search .......... None
   See application file for complete search history.

(56) References Cited

U.S. PATENT DOCUMENTS

| 6,576,743 B1 | 6/2003 | Conklin et al. |
| 2004/0236075 A1* | 11/2004 | Dumoutier et al. .......... 530/350 |

FOREIGN PATENT DOCUMENTS

| WO | WO-00/12708 | 3/2000 |
| WO | WO-0012708 A2 | 3/2000 |
| WO | WO-00/39161 | 7/2000 |
| WO | WO-0039161 A1 | 7/2000 |
| WO | WO-00/73457 | 12/2000 |
| WO | WO-00/78961 | 12/2000 |
| WO | WO-0073457 A1 | 12/2000 |
| WO | WO-0078961 A1 | 12/2000 |
| WO | WO-01/12672 | 2/2001 |
| WO | WO-0112672 A2 | 2/2001 |

(Continued)

OTHER PUBLICATIONS

Blumberg et al. Cell. Jan 12, 2001;104:9-19.*

(Continued)

*Primary Examiner*—Cherie M Woodward
(74) *Attorney, Agent, or Firm*—Darby & Darby P.C.; Aaron A. Schützer

(57) ABSTRACT

A soluble receptor that binds to IL-20 having two polypeptide subunits, IL-22R and IL-20RB. The two subunits are preferably linked together. In one embodiment one subunit is fused to the constant region of the light chain of an immunoglobulin, and the other subunit is fused to the constant region of the heavy chain of the immunoglobulin. The light chain and the heavy chain are connected via a disulfide bond.

11 Claims, 8 Drawing Sheets

FOREIGN PATENT DOCUMENTS

| WO | WO-02/058724 | 8/2002 |
| --- | --- | --- |
| WO | WO-02058724 A2 | 8/2002 |
| WO | WO-02/070001 | 9/2002 |
| WO | WO-02070001 A2 | 9/2002 |
| WO | WO-03/039444 | 5/2003 |
| WO | WO-03039444 A2 | 5/2003 |
| WO | WO-03/051384 | 6/2003 |
| WO | WO-03051384 A1 | 6/2003 |

OTHER PUBLICATIONS

Information Hyperlinked Over Proteins—"IHOP", IL-20RB, synonyms, last accessed Feb. 2008.*
Information Hyperlinked Over Proteins—"IHOP", IL-20RA, synonyms, last accessed Feb. 2008.*
Information Hyperlinked Over Proteins—"IHOP", IL-22R, synonyms, last accessed Feb. 2008.*
Asadullah et al., "Analysis of Cytokine Expression in Dermatololgy," *Arch. Dermatol.* 138:1189-1196, 2002.
Asadullah et al., "Interleukin-10 Therapy-Review of a New Approach," *Pharmacol. Rev.* 55:241-269, 2003.
Blumberg et al., "Interleukin 20: Discovery, Receptor Identification, and Role in Epidermal Function," *Cell* 104:9-19, 2001.
Cameron et al., "Cytokines and Chemokines-Their Receptors and Their Genes: An Overview," *Cytokines and Chemokines in Autoimmune Disease* 8-32, 2003.
Conti et al., "IL-10 subfamily members: IL-19, IL-20, IL-22 , IL-24 and IL-26," *Immunology Letters* 88:171-174, 2003.
Dumoutier et al., "Viral and cellular interleukin-10 (IL-10) related cytokines: from structures to functions," *Eur. Cytokine Netw* 13(2):5-15, 2002.
Fickenscher et al., "The interleukin-10 family of cytokines," *Trends in Immunology* 23(2):89-96, 2002.
Gröne, "Keratinocytes and cytokines," *Veterinary Immunol. Immunopathol.* 88:1-12, 2002.
Hosoi et al., "Lipopolysaccharide induces IL-20 expression in the primary cultured glial cells," The 75$^{th}$ Annual Meeting, Department of Pharmacology, Kumamoto University, Abstract P-112, 2002.
Huston et al., "Protein engineering of antibody binding sites: recovery of specific activity in an anti-digoxin single-chain Fv analogue produced in *Escherichia coli*," *Proc. Natl. Acad. Sci. USA.* 85(16): 5879-83 (1998).
Kotenko et al., "Identification of the Functional Interleukin-22 (IL-22) Receptor Complex," *J. Biol. Chem.* 276(4):2725-2732, 2001.
Kotenko, "The family of IL-10-related cytokines and their receptors: related, but to what extent," *Cytokine & Growth Factor Reviews* 13:223-240, 2002.
Last et al., "Use of EpiDerm as an Inflammatory Model for Preclinical Screening," Abstracts 119(1):325, 2002.
Liu et al., "IL-20 Specifically Stimulates the Proliferation of Human and Murine Multipotential Hematopoietic Progrnitors," *Blood* 100(11) :189a, Abstract #710, 2002.
Ozaki et al., "Cytokine and Cytokine Receptor Pleiotropy and Redundancy," *J. Biol. Chem.* 277(33):29355-29358, 2002.
Parrish-Novak et al., "Interleukins 19, 20, and 24 Signal through Two Distinct Receptor Complexes," *J. Biol. Chem.* 277(49):47517-47523, 2002.
Ramesh et al., "MDA-7/IL-24 is a Novel Ligand that Regulates Angiogenesis via the IL-22 Receptor," *Cancer Gene Therapy*, S3 (Dec. 12-14, 2002).
Rich et al., "Cytokines: IL-20—a new effector in skin inflammation," *Curr Biol.* 11(13):R531-534, 2001.
Rich, "IL-20: a new target for the treatment of inflammatory skin disease," *Expert Opin. Ther. Targets* 7(2):165-174, 2003.
Tachiiri et al , "Genomic structure and inducible expression of the IL-22 receptor α chain in mice," *Genes and Immunity* 4:153-159, 2003.
Vandenbroeck et al., "The Conserved Helix C Region in the Superfamily of Interferon-γ/Interleukin-10-related Cytokines Corresponds to a High-affinity Binding Site for the HSP70 Chaperone DnaK," *J. Biol. Chem.* 277(28):25668-25676, 2002.

Volk et al., "IL-10 and its homologs:important immune mediators and emerging immunotherapeutic agents," *Trends in Immunology* 22(8):414-417, 2001.
Walter, "Structure of Interleukin-10/Interleukin-10R1 Complex," *Immunologic Res.* 26(1-3):303-308, 2002.
Wolk et al., "Cutting Edge: Immune Cells as Sources and Targets of the IL-10 Family Members," *J. Immunol.* 5397-5402, 2002.
Xie et al., "Interleukin (IL)-22, a Novel Human Cytokine That Signals through the Interferon Receptor-related Proteins CRF2-4 and IL-22R," *J. Biol. Chem.* 275(40):31335-31339, 2000.
Xu et al., "A soluble class II cytokine receptor, IL-22RA2, is a naturally occurring IL-22 antagonist," *Proc. Natl. Acad. Sci. USA.* 98(17):9511-9516, 2001.
Asadullah et al.; "Analysis of Cytokine Express in Dermatology"; Arch. Dermatol. 138:1189-1196; 2002.
Asadullah et al.; "Interleukin-10 Therapy-Review of a New Approach"; Pharmacol. Rev. 55:241-269; 2003.
Blumberg et al.; "Interleukin 20: Discovery, Receptor Identification, and Role in Epidermal Function"; Cell; 104:9-19; 2001.
Cameron et al.; "Cytokines and Chemokines-Their Receptors and Their Genes: An Overview"; Cytokines and Chemokines in Autoimmune Disease 8-32; 2003.
Conti et al.; "IL-10 subfamily members: IL-19, IL-20, IL-22; IL-24 and IL-26"; Immunology Letters 88:171-174; 2003.
De Groot-Kruseman et al.; "Expression of the Novel Cytokine IL-21 During Acute Rejection After Clinical Heart Transplantation and the Effect of Immunosuppressive Agents"; Abstract P-2-1; Internal Medicine, Cardiology and Diagnostic Institute of Molecular Biology, Erasmus MC, Rotterdam, The Netherlands; J. Interferon Cytokine Res. 22(Suppl. 1); p. S-97; 2002.
Dumoutier et al.; "Viral and cellular interleukin-10 (IL-10) related cytokines: from structures to functions"; Eur. Cytokine Netw 13(2):5-15; 2002.
Fickenscher et al.; "The interleukin-10 family of cytokines"; Trends in Immunology 23(2):89-96; 2002.
Gröne; "Keratinocytes and cytokines"; Veterinary Immunol. Immunopathol.; 88:1-12; 2002.
He et al.; "Serum Amyloid a Induces IL-8 Secretion Through A G Protein-Coupled Receptor, FPRL1/LXA4R"; Abstract P-1-23; Department of Pharmacology, University of Illinois, Chicago, IL 60612, USA; J. Interferon Cytokine Res.; 22(Suppl. 1): p. S-97; 2002.
Hosoi et al.; "Lipopolysaccharide induces IL-20 expression in the primary cultured glial cells"; The 75th Annual Meeting, Department of Pharmacology, Kumamoto University, Abstract P-112; 2002.
Huston et al.; "Protein engineering of antibody binding sites: recovery of specific activity in an anti-digoxin single-chain Fv analogue produced in *Escherichia coli*"; Proc. Natl. Acad. Sci. USA; 85(16): 5879-83; 1998.
Kotenko et al.; "Identification of the Functional Interleukin-22 (IL-22) Receptor Complex"; J. Biol. Chem.; 276(4):2725-2732; 2001.
Kotenko; "The family of IL-10-related cytokines and their receptors: related, but to what extent"; Cytokine & Growth Factor Reviews; 12:223-240; 2002.
Kunz et al.; "Immune Cells as Sources and Targets of the Interleukin-10 Family Members"; Abstract P-2-3; J. Interferon Cytokine Res.; 22(Suppl. 1): p. S-97; 2002.
Last et al.; "Use of EpiDerm as an Inflammatory Model for Preclinical Screening"; Abstracts 119(1):325; 2002.
Liu et al.; "IL-20 Specifically Stimulates the Proliferation of Human and Murine Multipotential Hematopoietic Progmitors"; Blood; 100(11):189a; Abstract #710; 2002.
Musso et al.; "Role of IL-21 in the Differentiation of Human Dendritic Cells"; Abstract P-2-4; J. Interferon Cytokine Res. 22(Suppl. 1): p. S-98; 2002.
Ozaki et al.; "Cytokine and Cytokine Receptor Pleiotropy and Redundancy"; J. Biol. Chem. 277(33):29355-29358; 2002.
Parrish-Novak et al.; "Interleukins 19, 20, and 24 Signal through Two Distinct Receptor Complexes"; J. Biol. Chem.; 277(49):47517-47523; 2002.
Parrish-Novak et al.; "Overlapping Ligan Specificities but Divergent Function in the IL-20 Subfamily"; Abstract W-1-5; J. Interferon & Cytokine Res.; 22(Suppl. 1): p. S-46; 2002.

Pirhonen et al.; "Regulation of IL-12 and IL-23 Expression in Macrophages During Virus Infection"; Abstract P-2-6; J. Interferon Cytokine Res.; 22(Suppl. 1): p. S-98; 2002.

Ramesh et al.; "MDA-7/IL-24 is a Novel Ligand that Regulates Angiogenesis via the IL-22 Receptor"; Cancer Gene Therapy; S3 (Dec. 12-14, 2002).

Rich et al; "Cytokines: IL-20—a new effector in skin inflammation"; Curr Biol. 11(13):R531-534; 2001.

Rich; " IL-20: a new target for the treatment of inflammatory skin disease"; Expert Opin. Ther. Targets 7(2):165-174; 2003.

Stolina et al.; "Novel Neurotrophin-1/B Cell Stimulating Factor-3 (NNT-1/BSF-3) Stimulates Osteoblastic Cell Activities in Vitro Including Bone Formation and IL-6 Production"; Abstract P-2-7; J. Interferon Cytokine Res.; 22(Suppl. 1): pp. S-98-S-99; 2002.

Strengell et al.; "IL-21 Up-Regulates the Expression of Genes Associated with Innate Immunity and Th1 Response"; Abstract P-2-8; Dept. of Microbiology, National Public Health Institute, Helsinki, Finland and Department of Functional Cloning, ZymoGenetics, Seattle, Washington; J. Interferon Cytokine Res.; 22(Suppl. 1): p. S-99; 2002.

Tachiiri et al.; "Genomic structure and inducible expression of the IL-22 receptor α chain in mice"; Genes and Immunity; 4:153-159; 2003.

Vandenbroeck et al.; "The Conserved Helix C Region in the Superfamily of Interferon-γ/Interleukin-10-related Cytokines Corresponds to a High-affinity Binding Site for the HSP70 Chaperone DnaK"; J. Biol. Chem.; 277(28):25668-25676; 2002.

Volk et al.; "IL-10 and its homologs:important immune mediators and emerging immunotherapeutic agents"; Trends in Immunology; 22(8):414-417; 2001.

Walter; "Structure of Interleukin-10/Interleukin-10R1 Complex"; Immunologic Res.; 26(1-3):303-308; 2002.

Whitters et al.; "Phenotype of IL21R-/-Mice and Gene Expression Analysis Support a Role for Regulation of T and B Cell Responses by Interleukin 21"; Abstract P-2-11; Wyeth Research, Cambridge, MA; J. Interferon Cytokine Res.; 22(Suppl. 1): pp. S-99-S-100; 2002.

Witek et al.; "Primary Macrophages Express IL-21R and Respond to IL-21 by Proliferating and Secreting Increased Levels of Cytokines and Chemokines"; Abstract P-2-12; Wyeth Research; Cambridge, MA; J. Interferon Cytokine Res.; 22(Suppl. 1): p. S-100; 2002.

Wolk et al.; "Cutting Edge: Immune Cells as Sources and Targets of the IL-10 Family Members"; J. Immunol.; 5397-5402; 2002.

Xie et al.; Interleukin (IL)-22, a Novel Human Cytokine That Signals through the Interferon Receptor-related Proteins CRF2-4 and IL-22R; J. Biol. Chem.; 275(40):31335-31339; 2000.

Xu et al.; "A soluble class II cytokine receptor, IL-22RA2, is a naturally occurring IL-22 antagonist"; Proc. Natl. Acad. Sci. USA; 98(17):9511-9516, 2001.

* cited by examiner

US 7,704,950 B2

METHODS OF USING SOLUBLE HETERODIMERIC CYTOKINE RECEPTOR

This application is a continuation of U.S. patent application Ser. No. 10/471,151, which was filed Sep. 8, 2003 now abandoned as a U.S. National Phase Application pursuant to 35 U.S.C. 371 of International Application No. PCT/US02/07214 which was filed Mar. 7, 2002, claiming benefit of priority of U.S. Provisional application No. 60/274,560 which was filed Mar. 9, 2001 and U.S. Provisional application No. 60/299,865, which was filed Jun. 21, 2001. The entire disclosure of each of the foregoing applications is incorporated herein by reference.

BACKGROUND OF THE INVENTION

The teachings of all of the references cited herein are incorporated in their entirety herein by reference.

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type II cytokine receptor family (CRF2), based upon a characteristic 200 residue extracellular domain. The demonstrated in vivo activities of these interferons illustrate the enormous clinical potential of, and need for, other cytokines, cytokine agonists, and cytokine antagonists. Some cytokines are involved in the inflammatory cascade and can promote such diseases as rheumatoid arthritis, Crohn's disease, psoriasis, heart disease etc. Thus, there is a need to discover cytokines and their receptors that are involved in inflammation. One can then use the isolated soluble receptors of the cytokine to inhibit the cytokine-mediated inflammation.

DESCRIPTION OF THE INVENTION

Figure 1:
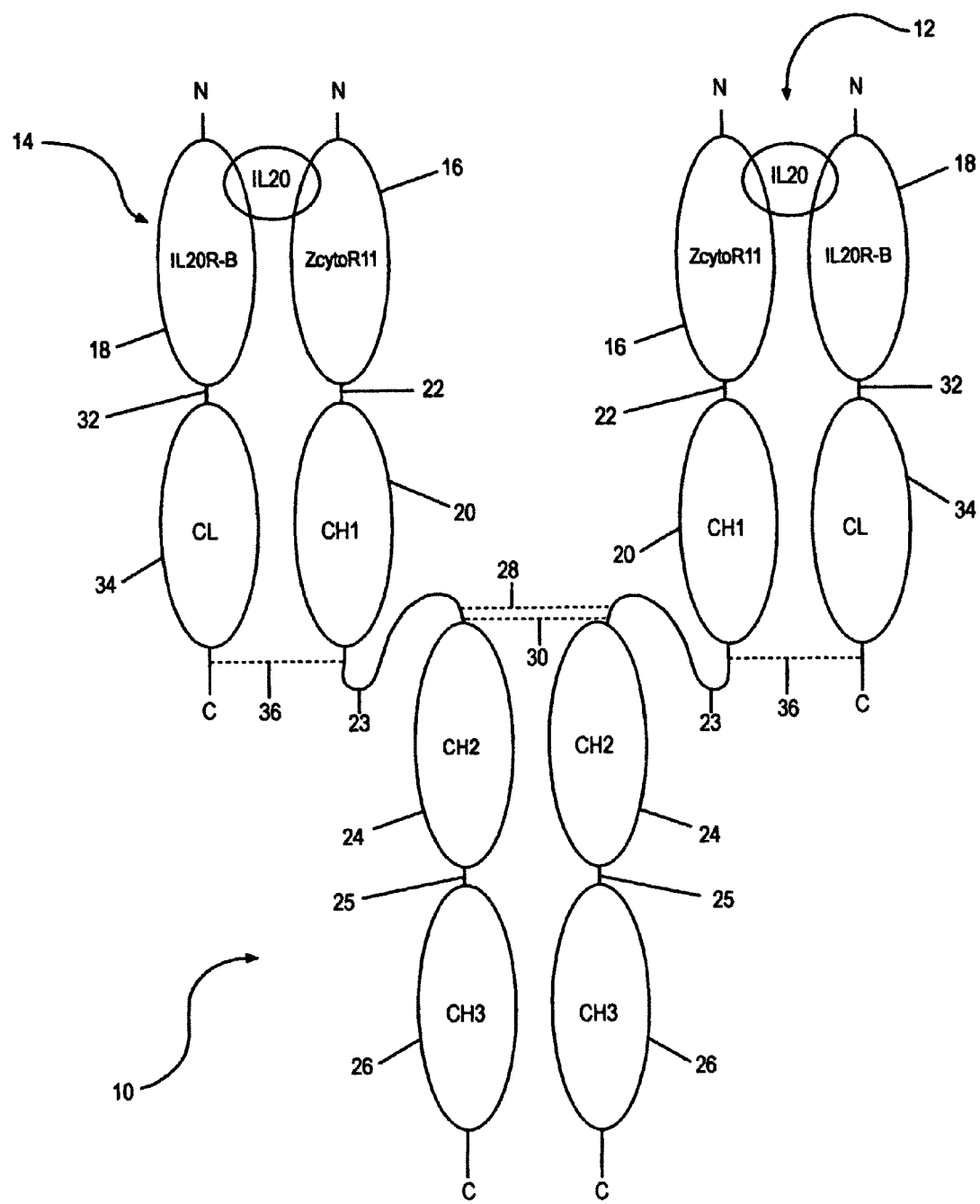
FIGS. 1-8 are schematic representations of different embodiments of the soluble receptor of the present invention

The present invention fills this need by providing a newly discovered soluble receptor that binds to Interleukin-20 (IL-20). The soluble receptor can be used to down-regulate IL-20 and thus treat inflammatory diseases such as psoriasis and inflammatory lung diseases.

IL-20 was formally called 'Zcyto10', (International Patent Publication No. WO 99/27103) and has the amino acid sequences of SEQ ID NOs: 1-9. A heterodimeric receptor that binds to IL-20 is comprised of two chains, an alpha chain and a beta chain. The alpha chain is referred to as IL-22R (formerly called Zcytor11). See U.S. Pat. No. 5,965,704. The beta chain, hereinafter referred to as IL-20RB, was formally called DIRS1. See International Patent Application No. PCT/US99/03735. The present invention is a soluble receptor comprised of the extracellular domain of IL-22R and the extracellular domain of IL-20RB.

The present invention encompasses an isolated soluble receptor comprised of a 'IL-22R' subunit and an 'IL-20RB' subunit, wherein the IL-22R subunit is comprised of a polypeptide having an amino acid sequence selected from the group consisting of SEQ ID NOs: 11, 12 and 13, and the IL-20RB subunit is comprised of a polypeptide having an amino acid sequence selected from the group consisting of SEQ ID NOs: 14-23. The IL-22R and IL-20RB subunits are generally linked together by a polypeptide linker. The linking can be by any means but generally by a peptide bond or a disulfide bond between a polypeptide connected to the IL-22R subunit and a polypeptide connected to the IL-20RB subunit. The present invention is also directed towards isolated polynucleotides that encode the novel IL-22R and IL-20RB polypeptides of the present invention.

In one embodiment the IL-22R subunit is fused to the constant region of the heavy chain of an immunoglobulin (Ig) molecule or a portion thereof and the IL-20RB subunit is fused to the constant region of the light chain of an Ig molecule such that the constant region of the light chain is disulfide bonded to the constant region of the heavy chain, generally to a cysteine residue on the hinge region of the heavy chain. Also the opposite can occur, the IL-22R subunit can be fused to the constant region of the light chain of an Ig molecule and the IL-20RB subunit can be fused to the constant region of the heavy chain of an Ig molecule.

In one embodiment of the soluble receptor of the present invention, the IL-22R subunit fused to the constant region of the heavy chain is comprised of an amino acid sequence selected from the group consisting of SEQ ID NOs: 25, 26, 31 and 32 and the IL-20RB subunit fused to the constant region of the light chain of the Ig molecule is comprised of an amino acid sequence selected from the group consisting of SEQ ID NOs: 28 and 29.

The present invention is further directed to a method for inhibiting interleukin-20 (IL-20) comprising administering to an individual a soluble IL-22R/IL-20RB heterodimeric polypeptide.

The present invention is also directed to a method for inhibiting IL-20 comprising administering to an antibody that binds to IL-22R.

The present invention is further directed to a polynucleotide encoding for the extracellular domain of IL-22R and the extracellular domain of IL-20RB. An example of such a polynucleotide is a vector or plasmid containing a polynucleotide that encodes for IL-22R and IL-20RB.

Definitions

Prior to setting forth the invention in more detail, it may be helpful to the understanding thereof to define the following terms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <$10^9$ M$^{-1}$.

The term "complements of a polynucleotide molecule" is a polynucleotide molecule having a complementary base sequence and reverse orientation as compared to a reference sequence.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78 (1985)).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nucleotides in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear, monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

As was stated above, IL-20 (formally called Zcyto10) is defined and methods for producing it and antibodies to IL-20 are contained in International Patent Application No. PCT/US98/25228, publication no. WO 99/27103, published Nov. 25, 1998 and U.S. patent application Ser. No. 09/313,458 filed May 17, 1999. The polynucleotide and polypeptide of human IL-20 are represented by SEQ ID NOs: 1-4, and mouse IL-20 by SEQ ID NOs: 5-9.

A receptor that binds to IL-20 has been discovered and is a heterodimer comprised of the polypeptide termed 'IL-22R' and a polypeptide termed 'IL-20RB'. The IL-22R, also called ZcytoR11, polypeptide, nucleic acid that encodes it, antibodies to IL-22R, and methods for producing it are disclosed in U.S. Pat. No. 5,965,704 issued Oct. 12, 1999. SEQ ID NOs: 10-12 are the IL-22R polynucleotides and polypeptides. The extracellular domain of the human IL-22R is comprised of either SEQ ID NO: 12 or SEQ ID NO: 13.

The extracellular domain of IL-20RB (SEQ ID NOs: 14-15, and a variant SEQ ID NOs: 22 and 23) is comprised of a polypeptide selected from the group consisting of SEQ ID NOs: 16-21. Preferably, the extracellular domain of the IL-22R polypeptide and the extracellular domain of the IL-20RB polypeptide are covalently linked together. In a preferred embodiment one extracellular subunit polypeptide has a constant region of a heavy chain of an immunoglobulin fused to its carboxy terminus and the other extracellular subunit has a constant light chain of an immunoglobulin (Ig) fused to its carboxy terminus such that the two polypeptides come together to form a soluble receptor and a disulfide bond is formed between the heavy and the light Ig chains. In another embodiment, a peptide linker could be fused to the two carboxy-termini of the polypeptides to form a covalently bonded soluble receptor.

SEQ ID NOs: 24 and 25 are constructs of the extracellular domain of IL-22R fused to a mutated human immunoglobulin gamma 1 constant region. SEQ ID NO: 26 is the predicted mature sequence without the signal sequence. SEQ ID NOs: 27 and 28 are constructs of the extracellular domain of IL-20RB fused to wild type human immunoglobulin kappa light chain constant region. SEQ ID NO: 29 is the predicted mature sequence without the signal sequence. FIG. 1 is a schematic representation of the heterotetramer.

SEQ ID NOs: 30 and 31 are constructs of the extracellular domain of IL-22R fused to a mutated human immunoglobulin gamma 1 constant region. SEQ ID NO: 32 is the predicted mature sequence without the signal sequence. SEQ ID NOs: 33 and 34 are constructs of the extracellular domain of IL-20RB fused to wild type human immunoglobulin kappa light chain constant region produced according to the procedure of example 12. SEQ ID NO: 35 is the predicted mature sequence without the signal sequence. The resultant heterotetramer does not have a polypeptide linker between the extracellular domains and the beginning of the Ig constant regions, 22 in FIG. 1. Hereinafter, the term "extracellular domain of a receptor" means the extracellular domain of the receptor or a portion of the extracellular domain that is necessary for binding to its ligand, in this case the ligand being IL-20.

One can link together the extracellular domains of IL-22R and IL-20RB in a number of ways such that the resultant soluble receptor can bind to IL-20. FIGS. 1-8 illustrate a representative number of embodiments of the present invention. Common elements in each of the drawings are given the same number. FIG. 1 represents the embodiment of the present invention of SEQ ID NOs: 24, 25, 26, 27, 28 and 29. The soluble receptor construct, designated 10, is comprised of two IL-20 binding site polypeptide chains designated 12 and 14. Each binding site is comprised of the extracellular domain of IL-22R, designated 16, and the extracellular domain of IL-20RB designated 18.

The extracellular domain, 16, of IL-22R is linked to the constant heavy one (CH1) domain, 20, of the human immunoglobulin gamma 1 heavy chain constant region via linker 22, which is SEQ ID NO: 36. The CH1 domain, 20, is then linked to the CH2 domain, 24, via hinge region 23. The CH2 domain, 24, is linked to the CH3 domain, 26, via hinge region 25.

Comparing the construct of FIG. 1 with SEQ ID NO:25, the mature extracellular domain, 16, of IL-22R extends from amino acid residues 18, a proline, to and including amino acid residue 228, a threonine of SEQ ID NO:25. Polypeptide linker, 22, extends from amino acid residue 229, a glycine to and including amino acid residue 243, a serine, of SEQ ID NO:25. The CH1 domain, 22 of FIG. 1, extends from amino acid residue 244, an alanine, to and including amino acid residue 341, a valine, of SEQ ID NO: 25. Hinge region 23 of FIG. 1 extends from amino acid residue 342, a glutamic acid to and including amino acid residue 356, a proline, of SEQ ID NO: 25. Chains 12 and 14 are disulfide-bonded together by means of disulfide bonds 28 and 30. The disulfide bonds are formed between the heavy chains by the cysteine residues at positions 352 and 356 of SEQ ID NO: 25 of each of the two heavy chains.

Extracellular domain, 18, of IL-20RB is linked to the constant region of the human kappa light chain (CL), 34 of FIG. 1 via polypeptide linker 32, which is the polypeptide SEQ ID NO: 36. The extracellular domain, 18, of IL-20RB extends from amino acid residue 30, a valine, to and including amino acid residue 230, an alanine, of SEQ ID NO: 28. Polypeptide linker, 32, extends from amino acid residue 231, a glycine, to and including amino acid residue 245, a serine, of SEQ ID NO: 28. The kappa constant light region, 34, extends from amino acid residue 246, an arginine, to and including the final amino acid residue 352, a cysteine, of SEQ ID NO: 28. The cysteine at position 352 of SEQ ID NO: 28 forms a disulfide bond, 36 in FIG. 1, with the cysteine at position 346 of SEQ ID NO: 25. The constant light chain 34 is thus linked to the hinge region, 23, by disulfide bond, 36. In this way, the extracellular domain, 16, of IL-22R is linked to the extracellular domain, 18, of IL-20RB to form a soluble receptor.

Figure 2:
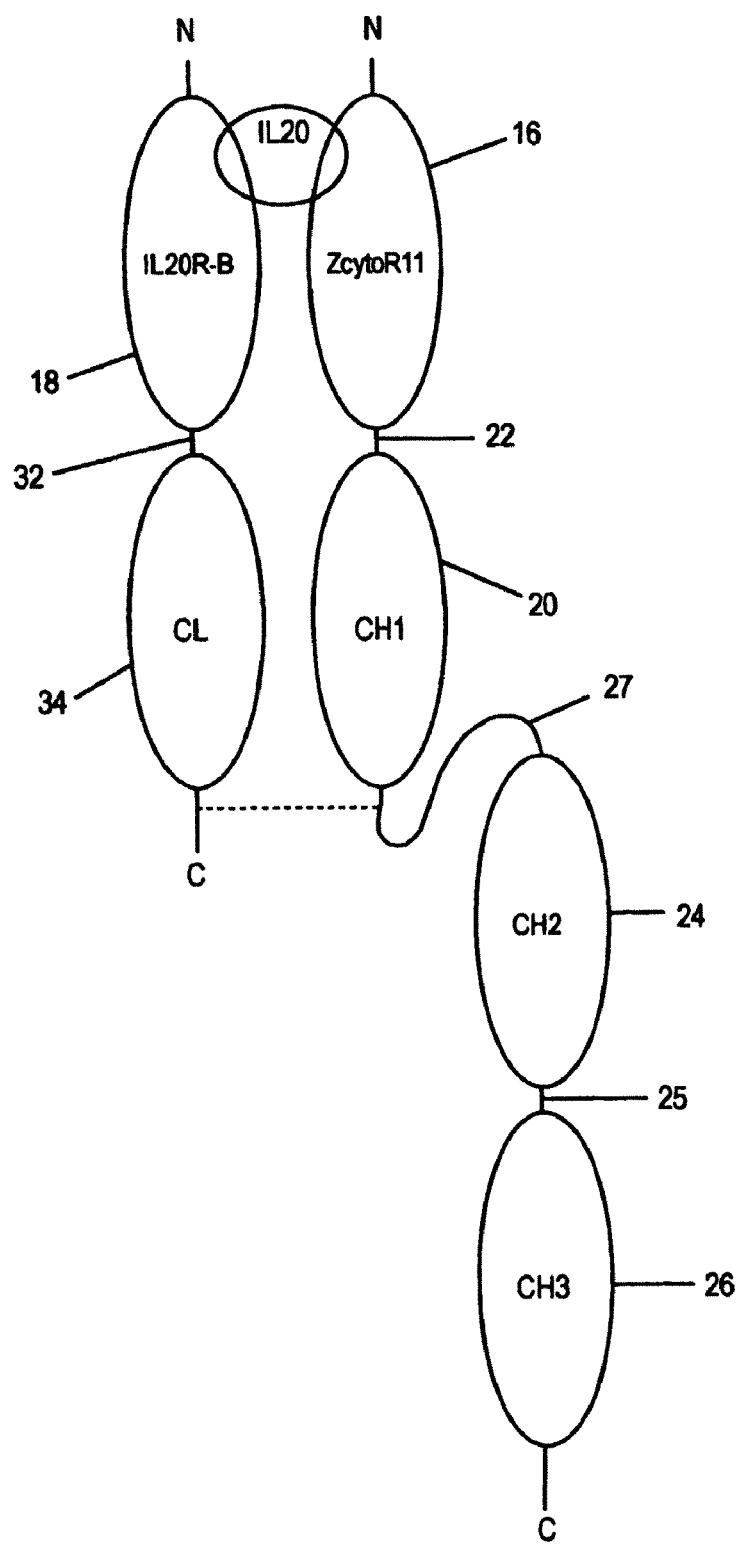

If the cysteine residues at positions 352 and 356 of SEQ ID NO: 25 were changed to different amino acid residues, the two IL-20 binding polypeptides, 12 and 14, would not be disulfide bonded together and would form a construct shown in FIG. 2 having hinge region, 27.

Figure 3:
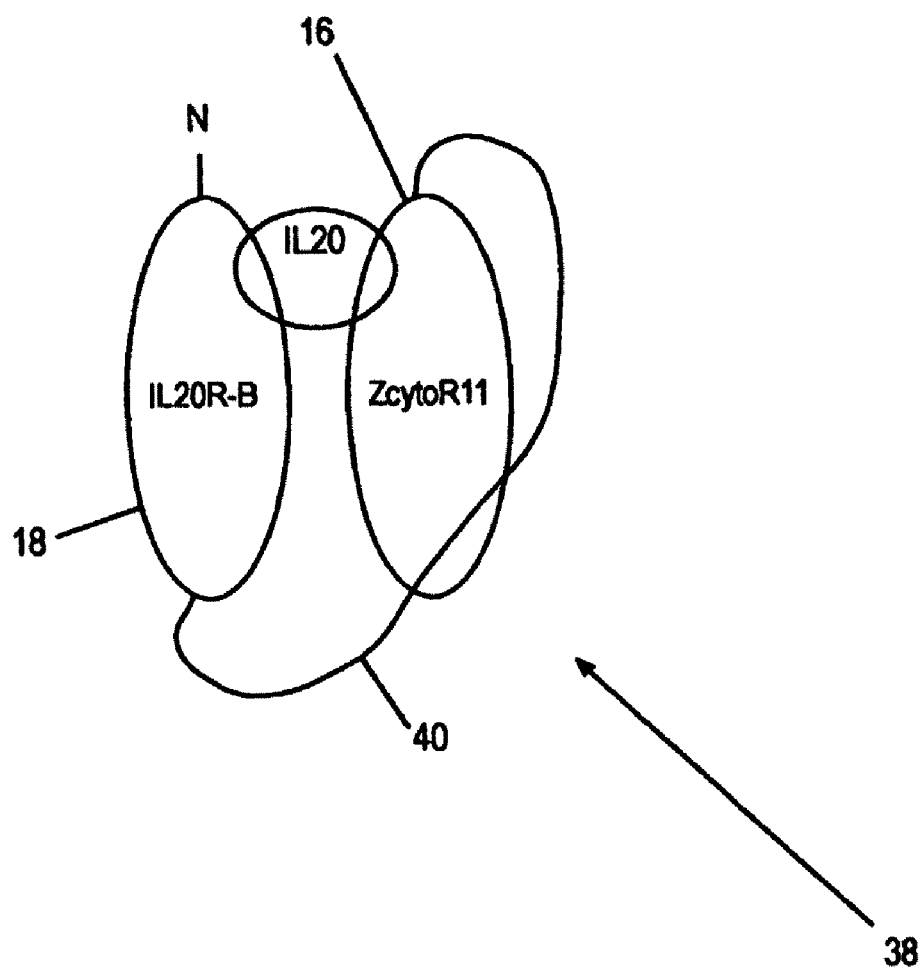

FIG. 3 shows a very simple soluble receptor 38 of the present invention wherein extracellular domain, 16, of IL-22R is connected to the extracellular domain, 18, of IL-20RB by means of a polypeptide linker, 40. The polypeptide linker extends from the amino terminus of extracellular domain, 16, of IL-22R and is connected to the carboxyl terminus of the extracellular domain, 18, of IL-20RB. The polypeptide linker should be between 100-240 amino acids in length, preferably about 170 amino acid residues in length. A suitable linker would be comprised of glycine and serine residues. A possible linker would be multiple units of SEQ ID NO: 36, preferably about 12.

Figure 4:
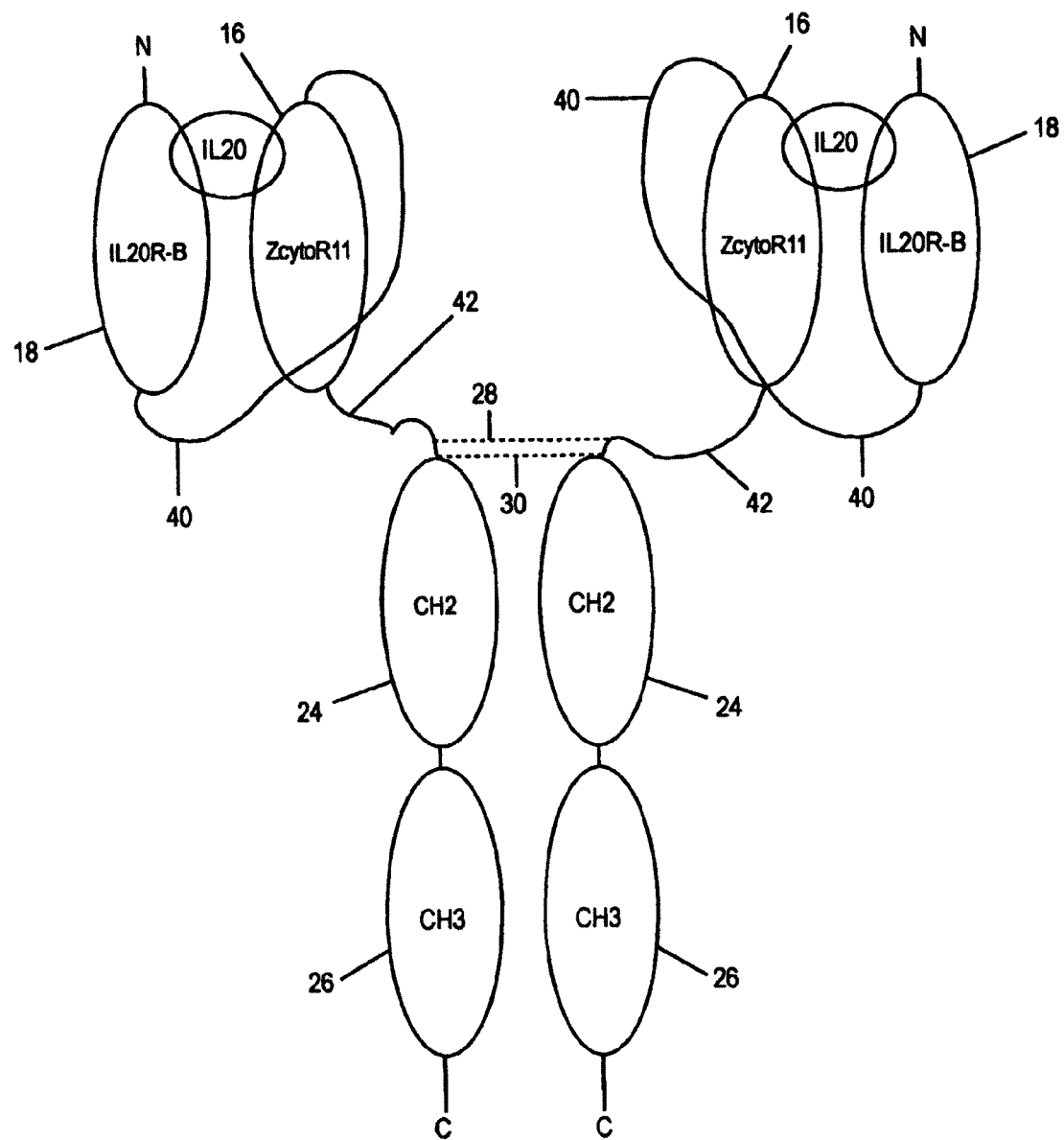

FIG. 4 shows an embodiment that has the extracellular domain, 16, of IL-22R linked to the extracellular domain, 18, of IL-20RB by means of linker 40, as in FIG. 3. While the extracellular domain, 16, of IL-22R is linked to the CH1 domain, 20, as in FIG. 1 by means of polypeptide linker 42, which should be about 30 amino acid residues in length. An ideal linker would be comprised of glycine and serine as in SEQ ID NO: 72, and the hinge sequence, 23 of FIG. 1.

Figure 5:
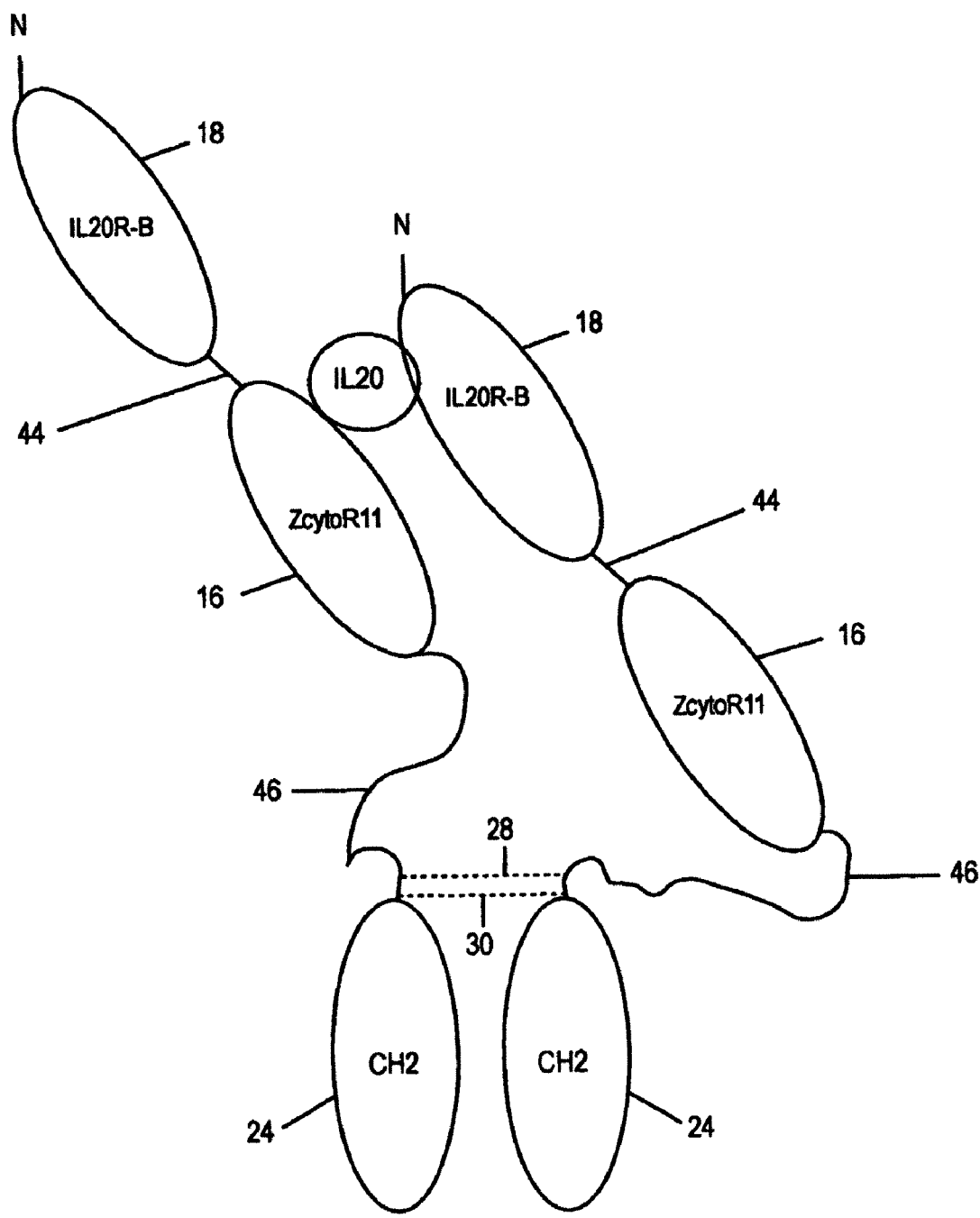

FIG. 5 shows another possible embodiment of the present invention. In this embodiment, a polypeptide linker 44 of about 15 amino acid residue, e.g. SEQ ID NO: 36, links the carboxyl terminus of the extracellular domain, 18, of IL-20RB with the amino terminus of the extracellular domain, 16, of IL-22R. A polypeptide linker 46 of about 30 amino acid residues extends from the carboxy terminus of the extracellular domain, 16, of IL-22R to the CH2 domain. The carboxyl terminus of linker 46 would preferably be comprised of the hinge region extending from amino acid residue 342, a glutamic acid to and including amino acid residue 356, a proline, of SEQ ID NO: 25. Nonetheless, polypeptide linker 46 would ideally have at least one cysteine residue at its carboxyl terminus so a disulfide bond could be formed.

Figure 6:
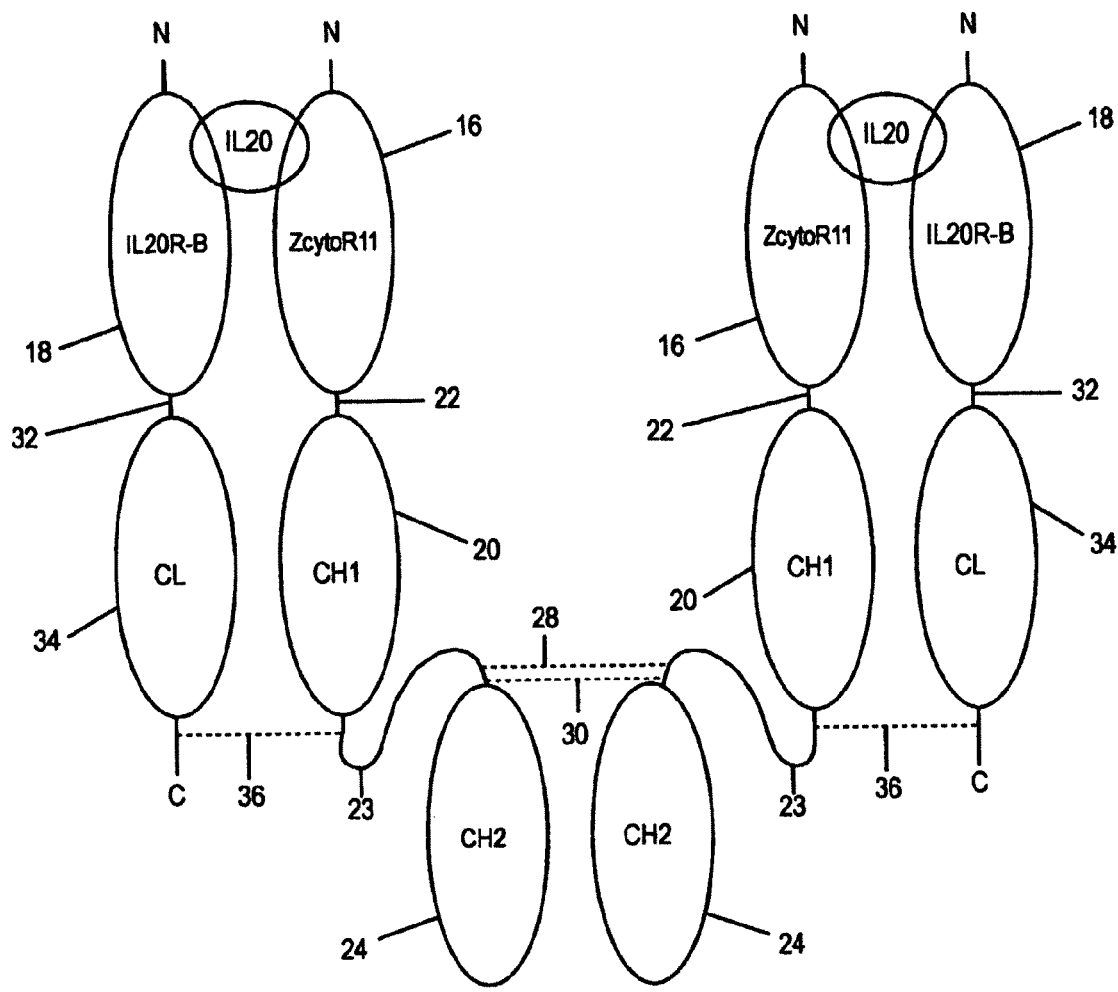

The soluble IL-20 receptor of FIG. 6 is identical to that of FIG. 1 except for the CH3 domain, 26 of FIG. 1, is not present on the embodiment of FIG. 6. The CH3 region begins at amino acid residue 467, a glycine, and extends to the last residue 573 of SEQ ID NO: 25.

Figure 7:
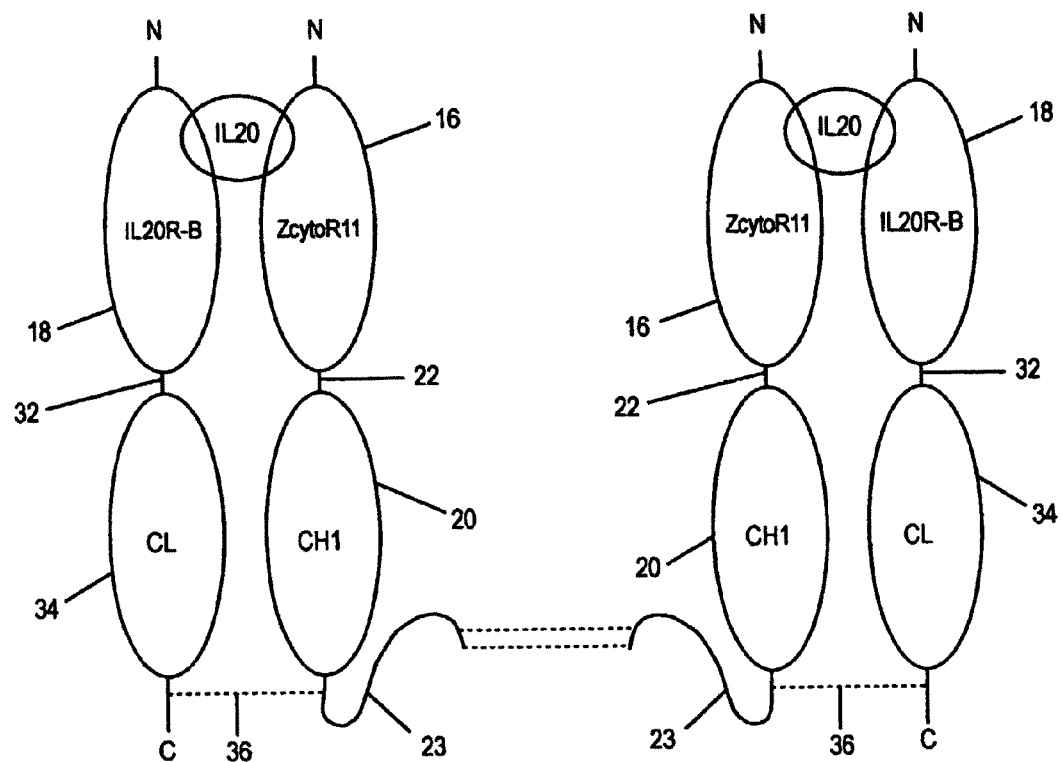

FIG. 7 shows a soluble IL-20 receptor construct that is identical to the construct of FIG. 1 except both the CH2, and CH3 domains are absent. The CH2 and CH3 domains run from amino acid residue 357, an alanine, to the end of the polypeptide sequence of SEQ ID NO: 25.

Figure 8:
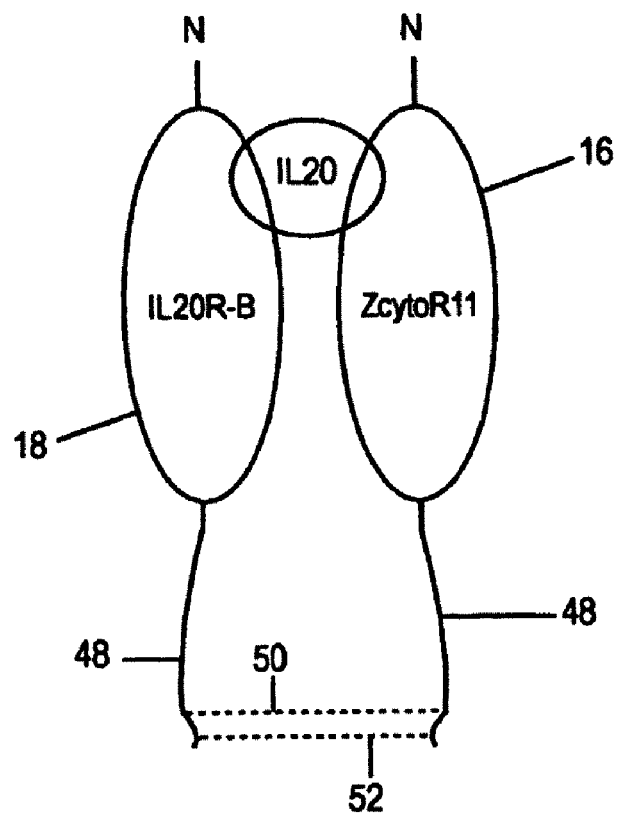

FIG. 8 shows a construct wherein both IL-22R, 16, and IL-20RB have a polypeptide linker, 48, fused to their respective carboxyl termini. Each polypeptide linker has two cysteine residues such that when they are expressed the cysteines form two disulfide bonds, 50 and 52. In this case the polypeptide linker is comprised of the hinge region, 23 in FIG. 1. The hinge region is comprised of amino acid residues 342, a glutamic acid, to and including amino acid residue 356 of SEQ ID NO: 25.

In another aspect of the invention, a method is provided for producing a soluble receptor comprised of extracellular domains of IL-22R and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-22R and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-20RB and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the secretion of a fusion protein comprised of the extracellular domain of IL-22R and IL-20RB; and (d) isolating the polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region.

In an alternative embodiment, a method is provided for producing a soluble receptor comprised of the extracellular domains of IL-22R and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-20RB and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-22R and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the production of a dimerized heterodimeric fusion protein comprised of the extracellular domain of IL-22R and IL-20RB; and (d) isolating the dimerized polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region. (See U.S. Pat. No. 5,843,725.)

In another embodiment, a method is provided for producing a soluble receptor comprised of the extracellular domains of IL-22R and IL-20RB comprising (a) introducing into a host cell a DNA construct containing a DNA construct that encodes the extracellular portion of IL-20RB and a DNA construct of the extracellular portion of IL-22R, (b) growing the host cell in an appropriate medium under physiological conditions to allow the production of the extracellular domain of IL-22R and the extracellular domain of IL-20RB; and (d) isolating the polypeptides from the host cell.

Other aspects of the present invention include host cells transformed or transfected with a DNA construct that encodes the extracellular domain of IL-22RB and a DNA construct that encodes the extracellular domain of IL-20RB. Both constructs can be on one vector or on separate vectors.

A polynucleotide, generally a cDNA sequence, encodes the described polypeptides herein. A cDNA sequence that encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT.
Cysteine (Cys) is encoded by TGC or TGT.
Aspartic acid (Asp) is encoded by GAC or GAT.
Glutamic acid (Glu) is encoded by GAA or GAG.
Phenylalanine (Phe) is encoded by TTC or TTT.
Glycine (Gly) is encoded by GGA, GGC, GGG or GGT.
Histidine (His) is encoded by CAC or CAT.
Isoleucine (Ile) is encoded by ATA, ATC or ATT.
Lysine (Lys) is encoded by AAA, or AAG.
Leucine (Leu) is encoded by TTA, TTG, CTA, CTC, CTG or CTT.
Methionine (Met) is encoded by ATG.
Asparagine (Asn) is encoded by AAC or AAT.

Proline (Pro) is encoded by CCA, CCC, CCG or CCT.

Glutamine (Gln) is encoded by CAA or CAG.

Arginine (Arg) is encoded by AGA, AGG, CGA, CGC, CGG or CGT.

Serine (Ser) is encoded by AGC, AGT, TCA, TCC, TCG or TCT.

Threonine (Thr) is encoded by ACA, ACC, ACG or ACT.

Valine (Val) is encoded by GTA, GTC, GTG or GTT.

Tryptophan (Trp) is encoded by TGG.

Tyrosine (Tyr) is encoded by TAC or TAT.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) that encodes the polypeptides of the president invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see, Grantham, et al., *Nuc. Acids Res.* 8:1893-1912 (1980); Haas, et al. *Curr. Biol* 6:315-324 (1996); Wain-Hobson, et al., *Gene* 13:355-364 (1981); Grosjean and Fiers, *Gene* 18:199-209 (1982); Holm, *Nuc. Acids Res.* 14:3075-3087 (1986); Ikemura, *J. Mol Biol* 158:573-597 (1982). As used herein, the term "preferential codon usage" or "preferential codons" is a term of art referring to protein translation codons that are most frequently used in cells of a certain species, thus favoring one or a few representatives of the possible codons encoding each amino acid. For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Sequences containing preferential codons can be tested and optimized for expression in various species, and tested for functionality as disclosed herein.

Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722 (1991); Ellman et al., *Methods Enzymol* 202:301 (1991; Chung et al., *Science* 259:806-809 (1993); and Chung et al., *Proc. Natl Acad Sci. USA* 90:10145-1019 (1993). In a second method, translation is carried out in *Xenopus oocytes* by microinjection of mutated mRNA and chemically aminoacylated suppressor tRNAs, Turcatti et al., *J. Biol Chem.* 271:19991-19998 (1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476 (1994). Naturally occurring amino acid residues can be converted to non-naturally occurring species by in vitro chemical modification. Chemical modification can be combined with site-directed mutagenesis to further expand the range of substitutions, Wynn and Richards, *Protein Sci.* 2:395-403 (1993).

A limited number of non-conservative amino acids, amino acids that are not encoded by the genetic code, non-naturally occurring amino acids, and unnatural amino acids may be substituted for amino acid residues.

Essential amino acids in the polypeptides of the present invention can be identified according to procedures known in the art, such as site-directed mutagenesis or alanine-scanning mutagenesis, Cunningham and Wells, *Science* 244: 1081-1085 (1989); Bass et al., *Proc. Natl. Acad. Sci. USA* 88:4498-502 (1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699-708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312 (1992); Smith et al., *J. Mol Biol* 224: 899-904 (1992); Wlodaver et al., *FEBS Lett.* 309:59-64 (1992).

Multiple amino acid substitutions can be made and tested using known methods of mutagenesis and screening, such as those disclosed by Reidhaar-Olson and Sauer, *Science* 241: 53-57 (1988) or Bowie and Sauer, *Proc. Natl. Acad. Sci. USA* 86:2152-2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display, e.g., Lowman et al., *Biochem.* 30:10832-10837 (1991); Ladner et al., U.S. Pat. No. 5,223,409; Huse, WIPO Publication WO 92/06204) and region-directed mutagenesis, Derbyshire et al., *Gene* 46:145 (1986); Ner et al., *DNA* 7:127 (1988).

Variants of the disclosed IL-20, IL-22R and IL-20RB DNA and polypeptide sequences can be generated through DNA shuffling as disclosed by Stemmer, *Nature* 370:389-391, (1994), Stemmer, *Proc. Natl. Acad. Sci. USA* 91:10747-10751 (1994) and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modem equipment. These methods allow the rapid determination of the importance of individual amino acid residues in a polypeptide of interest, and can be applied to polypeptides of unknown structure.

Protein Production

Polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., (Cold Spring Harbor Laboratory Press, Cold Spring Harbor, N.Y., 1989), and Ausubel et al., eds., *Current Protocols in Molecular Biology* (John Wiley and Sons, Inc., NY, 1987).

In general, a DNA sequence encoding a polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the native polypeptides, or may be derived from another secreted protein (e.g., t-PA) or synthesized de novo. The secretory signal sequence is operably linked to the DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection, Wigler et al., *Cell* 14:725 (1978), Corsaro and Pearson, *Somatic Cell Genetics* 7:603 (1981); Graham and Van der Eb, *Virology* 52:456 (1973), electroporation, Neumann et al., *EMBO J.* 1:841-845 (1982), DEAE-dextran mediated transfection (Ausubel et al., ibid., and liposome-mediated transfection, Hawley-Nelson et al., *Focus* 15:73 (1993); Ciccarone et al., *Focus* 15:80 (1993), and viral vectors, Miller and Rosman, *BioTechniques* 7:980 (1989); Wang and Finer, *Nature Med.* 2:714 (1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol* 36:59 (1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47 (1987). Transformation of insect cells and production of foreign polypeptides therein is disclosed by Guarino et al, U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding a polypeptide is inserted into the baculoviral genome in place of the AcNPV polyhedrin gene coding sequence by one of two methods. The first is the traditional method of homologous DNA recombination between wild-type AcNPV and a transfer vector containing the gene flanked by AcNPV sequences. Suitable insect cells, e.g. SF9 cells, are infected with wild-type AcNPV and transfected with a transfer vector comprising a polynucleotide operably linked to an AcNPV polyhedrin gene promoter, terminator, and flanking sequences. See, King, L. A. and Possee, R. D., *The Baculovirus Expression System: A Laboratory Guide*, (Chapman & Hall, London); O'Reilly, D. R. et al., *Baculovirus Expression*

Vectors: *A Laboratory Manual* (Oxford University Press, New York, N.Y., 1994); and, Richardson, C. D., Ed., *Baculovirus Expression Protocols. Methods in Molecular Biology*, (Humana Press, Totowa, N.J. 1995). Natural recombination within an insect cell will result in a recombinant baculovirus that contains coding sequences driven by the polyhedrin promoter. Recombinant viral stocks are made by methods commonly used in the art.

The second method of making recombinant baculovirus utilizes a transposon-based system described by Luckow, V. A. et al., *J Virol* 67:4566 (1993). This system is sold in the Bac-to-Bac kit (Life Technologies, Rockville, Md.). This system utilizes a transfer vector, pFastBac1™ (Life Technologies) containing a Tn7 transposon to move the DNA encoding the polypeptide into a baculovirus genome maintained in *E. coli* as a large plasmid called a "bacmid." The pFastBac1™ transfer vector utilizes the AcNPV polyhedrin promoter to drive the expression of the gene of interest. However, pFastBac1™ can be modified to a considerable degree. The polyhedrin promoter can be removed and substituted with the baculovirus basic protein promoter (also known as Pcor, p 6.9 or MP promoter), which is expressed earlier in the baculovirus infection, and has been shown to be advantageous for expressing secreted proteins. See, Hill-Perkins, M. S. and Possee, R. D., *J Gen Virol* 71:971 (1990); Bonning, B. C. et al., *J Gen Virol* 75:1551 (1994); and, Chazenbalk, G. D., and Rapoport, B., *J Biol Chem* 270:1543 (1995). In such transfer vector constructs, a short or long version of the basic protein promoter can be used. Moreover, transfer vectors can be constructed that replace the native secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native secretory signal sequence. In addition, transfer vectors can include an in-frame fusion with DNA encoding an epitope tag at the C- or N-terminus of the expressed polypeptide, for example, a Glu-Glu epitope tag, Grussenmeyer, T. et al., *Proc Natl Acad Sci.* 82:7952 (1985). Using a technique known in the art, a transfer vector containing a recombinant gene is transformed into *E. coli*, and screened for bacmids that contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses the polypeptide is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA* (ASM Press, Washington, D.C., 1994). Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. The recombinant virus-infected cells typically produce the recombinant polypeptide at 12-72 hours post-infection and secrete it with varying efficiency into the medium. The culture is usually harvested 48 hours post-infection. Centrifugation is used to separate the cells from the medium (supernatant). The supernatant containing the polypeptide is filtered through micropore filters, usually 0.45 µm pore size. Procedures used are generally described in available laboratory manuals (King, L. A. and Possee, R. D., ibid., O'Reilly, D. R. et al., ibid.; Richardson, C. D., ibid.). Subsequent purification of the polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986) and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art; see, e.g., Sambrook et al., ibid.). When expressing a polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient, which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Protein Isolation

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods* (Pharmacia LKB Biotechnology, Uppsala, Sweden, 1988).

Polypeptides can be isolated by exploitation of their properties. For example, immobilized metal ion adsorption (IMAC) chromatography can be used to purify histidine-rich proteins, including those comprising polyhistidine tags. Briefly, a gel is first charged with divalent metal ions to form a chelate, Sulkowski, *Trends in Biochem*. 3:1 (1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography. A protein fused to the Fc portion of an immunoglobulin can be purified using a 'Protein A column'. *Methods in Enzymol.*, Vol. 182, "Guide to Protein Purification", M. Deutscher, (ed.), page 529-539 (Acad. Press, San Diego, 1990). Within additional embodiments of the invention, a fusion of the polypeptide of interest and an affinity tag (e.g., maltose-binding protein, an immunoglobulin domain) may be constructed to facilitate purification.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

A variety of assays known to those skilled in the art can be utilized to detect antibodies that bind to protein or peptide. Exemplary assays are described in detail in *Antibodies: A Laboratory Manual*, Harlow and Lane (Eds.) (Cold Spring Harbor Laboratory Press, 1988). Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay.

The soluble receptors of the present invention can be used to down-regulate IL-20, which has been shown to be involved in a number of inflammatory processes. Specifically, IL-20 has been shown to up-regulate IL-8. Inflammatory diseases in which IL-8 plays a significant role, and for which a decrease in IL-8 would be beneficial are, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease. Thus, the soluble receptor to IL-20 of the present invention can be administered to a patient to treat these diseases.

Biology of IL-20, Its Receptor and Its R le in Psoriasis

Two orphan class II cytokine receptors, both of which are expressed in skin, were identified as IL-20 receptor subunits. Both IL-20 receptor subunits are required for ligand binding, distinguishing their role from that of subunits in the four other known class II cytokine receptors. IL-22R and IL-20RB are also coexpressed in a number of human tissues besides skin, including ovary, adrenal gland, testis, salivary gland, muscle, lung, kidney, heart and to a lesser degree the small intestine suggesting additional target tissues for IL-20 action. We conclude that the IL-20 heterodimeric receptor is structurally similar to other class II cytokine receptors and is expressed in skin where we have demonstrated activity of the IL-20 ligand.

Two lines of evidence indicate that a role IL-20 and its receptor are involved in psoriasis. This multigenic skin disease is characterized by increased keratinocyte proliferation, altered keratinocyte differentiation, and infiltration of immune cells into the skin. The first line of evidence for a role of IL-20 in psoriasis is that the observed hyperkeratosis and thickened epidermis in the transgenic mice that resemble human psoriatic abnormalities. Decreased numbers of tonofilaments, thought to be related to defective keratinization, are a striking feature of human psoriasis. Intramitochondrial inclusions have been found in both chemically induced and naturally occurring hyperplastic skin conditions in mice. The cause of the inclusions and their effects on mitochondrial function, if any, are unknown. We conclude that IL-20 transgenic mice exhibit many of the characteristics observed in human psoriasis.

Use of Antagonist to IL-20 to Treat Psoriasis

As indicated in the discussion above and the examples below, IL-20 is involved in the pathology of psoriasis. Thus, the soluble receptors of the present invention can be administered to an individual to down-regulate IL-20 and thus treat psoriasis.

Psoriasis is one of the most common dermatologic diseases, affecting up to 1 to 2 percent of the world's population. It is a chronic inflammatory skin disorder characterized by erythematous, sharply demarcated papules and rounded plaques, covered by silvery micaceous scale. The skin lesions of psoriasis are variably pruritic. Traumatized areas often develop lesions of psoriasis. Additionally, other external factors may exacerbate psoriasis including infections, stress, and medications, e.g. lithium, beta blockers, and anti-malarials.

The most common variety of psoriasis is called plaque type. Patients with plaque-type psoriasis will have stable, slowly growing plaques, which remain basically unchanged for long periods of time. The most common areas for plaque psoriasis to occur are the elbows knees, gluteal cleft, and the scalp. Involvement tends to be symmetrical. Inverse psoriasis affects the intertriginous regions including the axilla, groin, submammary region, and navel, and it also tends to affect the scalp, palms, and soles. The individual lesions are sharply demarcated plaques but may be moist due to their location. Plaque-type psoriasis generally develops slowly and runs an indolent course. It rarely spontaneously remits.

Eruptive psoriasis (guttate psoriasis) is most common in children and young adults. It develops acutely in individuals without psoriasis or in those with chronic plaque psoriasis. Patients present with many small erythematous, scaling papules, frequently after upper respiratory tract infection with beta-hemolytic streptococci. Patients with psoriasis may also develop pustular lesions. These may be localized to the palms and soles or may be generalized and associated with fever, malaise, diarrhea, and arthralgias.

About half of all patients with psoriasis have fingernail involvement, appearing as punctate pitting, nail thickening or subungual hyperkeratosis. About 5 to 10 percent of patients with psoriasis have associated joint complaints, and these are most often found in patients with fingernail involvement. Although some have the coincident occurrence of classic Although some have the coincident occurrence of classic rheumatoid arthritis, many have joint disease that falls into one of five type associated with psoriasis: (1) disease limited to a single or a few small joints (70 percent of cases); (2) a seronegative rheumatoid arthritis-like disease; (3) involvement of the distal interphalangeal joints; (4) severe destructive arthritis with the development of "arthritis mutilans"; and (5) disease limited to the spine.

Psoriasis can be treated by administering antagonists to IL-20. The preferred antagonists are either a soluble receptor to IL-20 or antibodies, antibody fragments or single chain antibodies that bind to either the IL-20 receptor or to IL-20. The antagonists to IL-20 can be administered alone or in combination with other established therapies such as lubricants, keratolytics, topical corticosteroids, topical vitamin D derivatives, anthralin, systemic antimetabolites such as methotrexate, psoralen-ultraviolet-light therapy (PUVA), etretinate, isotretinoin, cyclosporine, and the topical vitamin D3 derivative calcipotriol. The antagonists, in particularly the soluble receptor or the antibodies that bind to IL-20 or the IL-20 receptor can be administered to individual subcutaneously, intravenously, or transdermally using a cream or transdermal patch that contains the antagonist of IL-20. If administered subcutaneously, the antagonist can be injected into one or more psoriatic plaques. If administered transdermally, the antagonists can be administered directly on the plaques using a cream containing the antagonist to IL-20.

Use of Antagonists to IL-20 to Treat Inflammatory Conditions of the Lung.

A soluble receptor of IL-20 of the present invention can be administered to a person who has asthma, bronchitis or cystic fibrosis or other inflammatory lung disease to treat the disease. The antagonists can be administered by any suitable method including intravenous, subcutaneous, bronchial lavage, and the use of inhalant containing an antagonist to IL-20.

Administration of the IL-20 Soluble Receptor

The quantities of the IL-20 soluble necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 µg to 1000 µg per kilogram of body weight per day. A dosage for an average adult of the IL-20 soluble receptor would be about 25 mg given twice weekly as a subcutaneous injection. Injections could be given at the site of psoriatic lesions for the treatment of psoriasis. For subcutaneous or intravenous administration of the antagonist to IL-20, the antibody or soluble receptor can be in phosphate buffered saline. Also in skin diseases such as psoriasis, the antagonist to IL-20 can be administered via an ointment or transdermal patch. The doses by may be higher or lower as can be determined by a medical doctor with ordinary skill in the art. For a complete discussion of drug formulations and dosage ranges see *Remington's Pharmaceutical Sciences*, 18$^{th}$ Ed., (Mack Publishing Co., Easton, Penn., 1996), and *Goodman and Gilman's: The Pharmacological Bases of Therapeutics*, 9$^{th}$ Ed. (Pergamon Press 1996).

The invention is further illustrated by the following non-limiting examples:

Example 1

Up-Regulation of IL-8 by IL-20

Methods:

Normal Human Epidermal neonatal keratinocytes (NHEK) (from Clonetics) at passage 2 were plated and grown to confluency in 12 well tissue culture plates. KGM (Keratinocyte growth media) was purchased from Clonetics. When cells reached confluency, they were washed with KGM media minus growth factors=KBM (keratinocyte basal media). Cells were serum starved in KBM for 72 hours prior to the addition of test compounds. Thrombin at 1 I.U./mL and trypsin at 25 nM were used as positive controls. One mL of media/well was added. KBM only was used as the negative control.

IL-20 was made up in KBM media and added at varying concentrations, from 2.5 µg/ml down to 618 ng/mL in a first experiment and from 2.5 µg/mL down to 3 ng/mL in a second experiment.

Cells were incubated at 37° C., 5% $CO_2$ for 48 hours. Supernatants were removed and frozen at −80° C. for several days prior to assaying for IL-8 and GM-CSF levels. Human IL-8 Immunoassay kit # D8050 (RandD Systems, Inc.) and human GM-CSF Immunoassay kit # HSGMO (RandD Systems, Inc.) were used to determine cytokine production following manufacturer's instructions.

Results

The results indicated that the expression of IL-8 and GM-CSF were induced by IL-20.

Example 2

Cloning of IL-20RB

Cloning of IL-20RB Coding Region

Two PCR primers were designed based on the sequence from International Patent Application No. PCT/US99/03735 (publication no. WO 99/46379) filed on Mar. 8, 1999. SEQ ID NO: 38 contains the ATG (Met1) codon with an EcoRI restriction site, SEQ ID NO: 37 contains the stop codon (TAG) with an XhoI restriction site. The PCR amplification was carried out using a human keratinocyte (HaCaT) cDNA library DNA as a template and SEQ ID NO: 37 and SEQ ID NO: 38 as primers. The PCR reaction was performed as follows: incubation at 94° C. for 1 min followed by 30 cycles of 94° C. for 30 sec and 68° C. for 2 min, after additional 68° C. for 4 min, the reaction was stored at 4° C. The PCR products were run on 1% Agarose gel, and a 1 kb DNA band was observed. The PCR products were cut from the gel and the DNA was purified using a QIAquick Gel Extraction Kit (Qiagen). The purified DNA was digested with EcoRI and XhoI, and cloned into a pZP vector that was called pZP7N. A pZP plasmid is a mammalian expression vector containing an expression cassette having the mouse metallothionein-1 promoter, human tPA leader peptide, multiple restriction sites for insertion of coding sequences, a Glu-Glu tag, and a human growth hormone terminator. The plasmid also has an *E. coli* origin of replication, a mammalian selectable marker expression unit having an SV40 promoter, an enhancer and an origin of replication, as well as a DHFR gene, and the SV40 terminator. Several IL-20RB-pZP7N clones were sequenced. They all contain three non-conservative mutations compared with the sequence of IL-20RB in PCT/US99/03735: (sequence IL-20RB-pZP7N), 146 Pro (CCC)—Thr (ACC), 148 His (CAT)—Asp (GAT), and 171 Thr (ACG)—Arg (AGG).

To verify the three substitutions in IL-20RB-pZP7N clone, PCR amplification was carried out using three difference cDNA sources—fetal skin marathon cDNA, HaCaT cDNA library DNA, and prostate smooth muscle cDNA library DNA—as templates. The PCR products were gel purified and sequenced. The sequence of each of the three PCR products was consistent with that of the IL-20RB-pZP7N clone. IL-20RB is SEQ ID NO: 22 and 23, and the mature extracellular domain is SEQ ID NO: 21.

Example 3

Binding of IL-20 to IL-20RB/IL-22R Heterodimer

A cell-based binding assay was used to verify IL-20 binds to IL-22R- IL-20RB heterodimer.

Expression vectors containing known and orphan Class II cytokine receptors (including IL-22R and IL-20RB) were transiently transfected into Baf3 cells.

Plated cells out at 5000 cells/well, treated cells with IL-20 (zcyto10), MDA-7, and Soluble Proteins.

Inc. at 37 degrees for 3 days (72 hrs.)

Added 20 ul/well of Alamar Blue, inc. at 37 degrees overnight (24 hrs.)

Read on the f-Max (Molecular Devises) in the Robotics room on 544 excitation/590 emission setting.

Results:

Positive proliferative response with treatments of IL-20 (zcyto10) and MDA-7 from 0.1 ng/ml to 100 ng/ml on Baf3/DIRS1/ZcytoR11 cell line.

A neutralization of the positive proliferative response of IL-20 and MDA-7 (same conc.'s) when IL-20 and MDA-7 were treated in combination with the IL-22R Soluble Receptor (heterodimeric Sol. R.) at a 60 fold molar excess.

A neutralization of the positive proliferative response of MDA-7 (from 0.1 to 10 ng/ml) when MDA-7 was treated in combination with IL-20RB Soluble Protein (thrombin cleaved version) at a 60 fold molar excess.

Example 4

Up-Regulation of Inflammatory Cytokines by IL-20

Cell Treatment

The human keratinocyte cell line, HaCaT was grown at 37° C. to several days post-confluence in T-75 tissue culture flasks. At this point, normal growth media (DMEM+10% FBS) was removed and replaced with serum-free media. Cells were then incubated for two days at 37° C. DMEM was then removed and four flasks of cells per treatment were treated with one of each of the following conditions for four hours at 37° C.: recombinant human (rh) IL-1 alpha at 5 ng/mL, rh IL-1 alpha at 20 ng/mL, rh IL-1 alpha at 5 ng/mL+IL-20 at 1 µg/mL, IL-20 at 1 µg/mL, or rh IL-10 at 10 ng/mL.

RNA Isolation

Following cytokine treatment, media was removed and cells were lysed using a guanidium thiocyanate solution. Total RNA was isolated from the cell lysate by an overnight spin on a cesium chloride gradient. The following day, the RNA pellet was resuspended in a TE/SDS solution and ethanol precipitated. RNA was then quantitated using a spectrophotometer, followed by a DNase treatment as per Section V.B. of Clontech's Atlas™ cDNA Expression Arrays User Manual (version PT3140-1/PR9X390, published Nov. 5, 1999. Quality of RNA samples was verified by purity calculations based on spec readings, and by visualization on agarose gel. Genomic contamination of the RNA samples was ruled out by PCR analysis of the beta-actin gene.

Clontech's protocols for polyA+ enrichment, probe synthesis and hybridization to Atlas™ arrays were followed (see above, plus Atlas™ Pure Total RNA Labeling System User Manual, PT3231-1/PR96157, published Jun. 22, 1999. Briefly, polyA+RNA was isolated from 50 mg of total RNA using streptavidin coated magnetic beads (by Clontech, Paolo Alto, Calif.) and a magnetic particle separator. PolyA+RNA was then labeled with $^{alpha32}$P-dATP via RT-PCR. Clontech CDS primers specific to the 268 genes on the Atlas™ human cytokine/receptor array (Cat. #7744-1) were used in the reaction. Labeled probe was isolated using column chromatography and counted in scintillation fluid.

Array Membrane Hybridization

Atlas™ arrays were pre-hybridized with Clontech ExpressHyb plus 100 mg/nL heat denatured salmon sperm DNA for at least thirty minutes at 68° C. with continuous agitation. Membranes were then hybridized with $1.9 \times 10^6$ CPM/mL (a total of $1.14 \times 10^7$ CPM) overnight at 68° C. with continuous agitation. The following day, membranes were washed for thirty minutes×4 in 2×SSC, 1% SDS at 68° C., plus for thirty minutes×1 in 0.1×SSC, 0.5% SDS at 68° C., followed by one final room temperature wash for five minutes in 2×SSC. Array membranes were then placed in Kodak plastic pouches sealed and exposed to a phosphor imager screen overnight at room temperature. The next day, phosphor screens were scanned on a phosphor imager and analyzed using Clontech's AtlasImage™ 1.0 software.

Results

Genes Up-Regulated by IL-20
1. Tumor necrosis factor (TNF) was up-regulated 1.9-2.4 fold by IL-20.
2. Placental growth factors 1 & 2 (PLGF) were up-regulated 1.9-2.0 fold by IL-20.
3. Coagulating factor II receptor was up-regulated 2.0-2.5 fold by IL-20.
4. Calcitonin receptor was up-regulated 2.2-2.3 fold by IL-20.
5. TNF-inducible hyaluronate-binding protein TSG-6 was up-regulated 2.1-2.2 fold by IL-20.
6. Vascular endothelial growth factor (VEGF) receptor-1 precursor, tyrosine-protein kinase receptor (FLT-1) (SFLT) was up-regulated 2.1-2.7 fold by IL-20.
7. MRP-8 (calcium binding protein in macrophages MIF-related) was up-regulated 2.9-4.1 fold by IL-20.
8. MRP-14 (calcium binding protein in macrophages MIF-related) was up-regulated 3.0-3.8 fold by IL-20.
9. Relaxin H2 was up-regulated 3.14 fold by IL-20.
10. Transforming growth factor beta (TGFβ) receptor III 300 kDa was up-regulated 2.4-3.6 fold by IL-20.

Genes Showing Synergy with IL-20+IL-1 Treatment
1. Bone morphogenic protein 2a was up-regulated 1.8 fold with IL-20 treatment alone, 2.5 fold with IL-1 treatment alone, and 8.2 fold with both IL-20 and IL-1 treatment together.
2. MRP-8 was up-regulated 2.9 fold with IL-20 treatment alone, 10.7 fold with IL-1 treatment alone and 18.0 fold with both IL-20 and IL-1 treatment together.
3. Erythroid differentiation protein (EDF) was up-regulated 1.9 fold with IL-20 treatment alone, 9.7 fold with IL-1 treatment alone and 19.0 fold with both IL-20 and IL-1 treatment together.
4. MRP-14 (calcium binding protein in macrophages, MIF related) was up-regulated 3.0 fold with IL-20 treatment alone, 12.2 fold with IL-1 treatment alone and 20.3 fold with both IL-20 and IL-1 treatment together.
5. Heparin-binding EGF-like growth factor was up-regulated 2.0 fold with IL-20 treatment alone, 14 fold with IL-1 treatment alone and 25.0 fold with both IL-20 and IL-1 treatment together.
6. Beta-thromboglobulin-like protein was up-regulated 1.5 fold with IL-20 treatment alone, 15 fold with IL-1 treatment alone and 27 fold with both IL-20 and IL-1 treatment together.
7. Brain-derived neurotrophic factor (BDNF) was up-regulated 1.7 fold with IL-20 treatment alone, 25 fold with IL-1 treatment alone and 48 fold with both IL-20 and IL-1 treatment together.
8. Monocyte chemotactic and activating factor MCAF was up-regulated 1.3 fold with IL-20 treatment alone, 32 fold with IL-1 treatment alone and 56 fold with both IL-20 and IL-1 treatment together.

Example 5

IL-20 Transgenic Phenotype

Both human and mouse IL-20 were overexpressed in transgenic mice using a variety of promoters. The liver-specific mouse albumin promoter, directing expression of human IL-20, was used initially in an attempt to achieve circulating levels of protein. Subsequent studies were conducted using the keratin 14 (K14) promoter, which primarily targets expression to the epidermis and other stratified *squamous*

*epithelia*; the mouse metallothionein-1 promoter, which gives a broad expression pattern; and the EμLCK promoter, which drives expression in cells of the lymphoid lineage. Similar results were obtained in all four cases, possibly because these promoters all give rise to circulating levels of IL-20.

In all cases, transgenic pups expressing the IL-20 transgene were smaller than non-transgenic littermates, had a shiny appearance with tight, wrinkled skin and died within the first few days after birth. Pups had milk in their stomachs indicating that they were able to suckle. These mice had swollen extremities, tail, nostril and mouth regions and had difficulty moving. In addition, the mice were frail, lacked visible adipose tissue and had delayed ear and toe development. Low expression levels in liver (less than 100 mRNA molecules/cell) were sufficient for both the neonatal lethality and skin abnormalities. Transgenic mice without a visible phenotype either did not express the transgene, did not express it at detectable levels, or were mosaic.

Histologic analysis of the skin of the IL-20 transgenic mice showed a thickened epidermis, hyperkeratosis and a compact stratum corneum compared to non-transgenic littermates. Serocellular crusts (scabs) were observed occasionally. Electron microscopic (EM) analysis of skin from transgenic mice showed intramitochondrial lipoid inclusions, mottled keratohyaline granules, and relatively few tonofilaments similar to that observed in human psoriatic skin and in mouse skin disease models. In addition, many of the transgenic mice had apoptotic thymic lymphocytes. No other abnormalities were detected by histopathological analysis. These histological and EM results support and extend the observed gross skin alterations.

Example 6

Experimental Procedures

Luciferase Assay

Luciferase reporter assays were performed using BHK cells stably transfected with IL-22R and IL-20RB and utilizing the STAT-driven luciferase reporter cassette. Cells were switched to serum-free medium overnight prior to treatment with serial dilutions of IL-19, IL-20, and MDA-7 in the presence or absence of IL-20RA/IL-2ORB soluble receptor. Cells were lysed and read on the Berthold MicroLumat Plus for luciferase reporter activity.

BaF3 Proliferation Assay

Proliferation assays used Alamar Blue, which was added to the cells 24 h prior to being read on fmax plate reader (Molecular Devices, Sunnyvale, Calif.) using the Softmax Pro program.

RT-PCR Analysis on Human Tissues

RT-PCR was performed on a human Rapid-Scan gene expression panel (Origene Technologies, Inc.) using primers 5'-ccccagacacggtctacagcat-3' and 5'-gggtcaggccgaagaact-catat-3' to amplify a 440 bp fragment of human IL22R. PCR conditions are 94° C. for 2 min., followed by 35 cycles of 94° C. for 15 sec., 72° C. for 90 sec, then a final extension step of 72° C. for 2 min.

Results:

Since IL-22R is a shared alpha subunit, we evaluated an Origene panel for the expression of IL-22R mRNA. The highest IL-22R expression was detected in the pancreas, with skin and lung also exhibiting strong expression.

To test the possibility that the IL-20 subfamily might activate other Class II receptor combinations, BaF3 cells were stably transfected with Class II receptor subunits alone or in combinations and treated with the ligands. The assay shows that both IL-20 and MDA-7 stimulate an additional receptor complex consisting of consisting of IL-22R/IL-20RB (Table 1). We next wanted to determine which soluble receptors could block ligand activity. As mentioned above, IL-20RA/IL-20RB heterodimeric soluble receptor blocked proliferation stimulated by IL-20, IL-19, and MDA-7. In addition, IL-20RB soluble receptor alone blocked the activity of IL-19 and MDA-7, but not IL-20.

Since IL-22R is a shared alpha subunit, we evaluated an Origene panel for the expression of IL-22R mRNA (Table 2). The highest expression was detected in the pancreas, with skin and lung also exhibiting strong expression. Thus, overall IL-20Rα, IL-20Rβ, and IL-22R all have robust expression in skin and lung.

Since IL-20Rα, IL-20Rβ, and IL-22R are all expressed in the lung, we used in situ hybridization to evaluate whether the same cell types expressed all three receptors. FIG. 3 shows that both epithelial cells as well as immune infiltrates exhibit positive staining in lung sections tested for mRNA expression by in situ hybridization.

---

What is claimed is:

1. A method for inhibiting interleukin-20 (IL-20) in an individual comprising administering to said individual an effective dose of a soluble IL-22R/IL-20RB heterodimeric polypeptide, wherein said heterodimeric polypeptide comprises an IL-22R extracellular domain covalently linked to an IL-20RB extracellular domain, thereby inhibiting IL-20 in the individual.

2. The method of claim 1, wherein an immunoglobulin heavy chain constant region is linked to the carboxy terminus of the IL-22R extracellular domain and wherein an immunoglobulin light chain constant region is linked to the carboxy terminus of the IL-20RB extracellular domain.

3. The method of claim 1, wherein an immunoglobulin light chain constant region is linked to the carboxy terminus of the IL-22R extracellular domain and wherein an immunoglobulin heavy chain constant region is linked to the carboxy terminus of the IL-20RB extracellular domain.

4. The method of claim 1, wherein both the IL-22R extracellular domain and the IL-20RB extracellular domain have a peptide linker fused to their respective carboxy termini, wherein each of the peptide linkers has two cysteine residues so as to form two disulfide bonds between the peptide linkers, thereby forming a covalently bonded soluble receptor.

5. A method of treating an IL-8-mediated inflammatory disease in a subject, wherein the inflammatory disease is selected from the group consisting of adult respiratory disease (ARD), septic shock, multiple organ failure, asthma, bronchitis, bacterial pneumonia, psoriasis, eczema, atopic dermatitis, contact dermatitis, and inflammatory bowel disease, the method comprising administering to said subject an effective dose of a composition comprising a soluble IL-22R/IL-20RB heterodimeric polypeptide, wherein said heterodimeric polypeptide comprises an IL-22R extracellular domain covalently linked to an IL-20RB extracellular domain, thereby treating the disease.

6. The method of claim 5, wherein said inflammatory bowel disease is ulcerative colitis or Crohn's disease.

7. A method of treating an IL-20-mediated disease in a subject, wherein the IL-20-mediated disease is selected from the group consisting of asthma, bronchitis, and cystic fibrosis, the method comprising administering to said subject an effective dose of a composition comprising a soluble IL-22R/IL-20RB heterodimeric polypeptide, wherein said heterodimeric polypeptide comprises an IL-22R extracellular domain covalently linked to an IL-20RB extracellular domain, thereby treating the disease.

8. The method of claim 7, wherein an immunoglobulin heavy chain constant region is linked to the carboxy terminus of the IL-22R extracellular domain and wherein an immunoglobulin light chain constant region is linked to the carboxy terminus of the IL-20RB extracellular domain.

9. The method of claim 7, wherein an immunoglobulin light chain constant region is linked to the carboxy terminus of the IL-22R extracellular domain and wherein an immunoglobulin heavy chain constant region is linked to the carboxy terminus of the IL-20RB extracellular domain.

10. The method of claim 7, wherein both the IL-22R extracellular domain and the IL-20RB extracellular domain have a peptide linker fused to their respective carboxy termini, wherein each of the peptide linkers has two cysteine residues so as to form two disulfide bonds between the peptide linkers, thereby forming a covalently bonded soluble receptor.

11. A method of treating psoriasis in a subject, the method comprising administering to said subject an effective dose of a composition comprising a soluble IL-22R/IL-20RB heterodimeric polypeptide, wherein said heterodimeric polypeptide comprises an IL-22R extracellular domain covalently linked to an IL-20RB extracellular domain, thereby treating the psoriasis.

* * * * *

SEQUENCE LISTING

<160> NUMBER OF SEQ ID NOS: 40

<210> SEQ ID NO 1
<211> LENGTH: 176
<212> TYPE: PRT
<213> ORGANISM: Homo sapiens

<400> SEQUENCE: 1

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Asp
        35                  40                  45

-continued

```
Ile Arg Gly Ser Val Gln Ala Lys Asp Gly Asn Ile Asp Ile Arg Ile
        50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                    85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
            115                 120                 125

His Met Thr Cys His Cys Gly Glu Glu Ala Met Lys Lys Tyr Ser Gln
        130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                    165                 170                 175

<210> SEQ ID NO 2
<211> LENGTH: 152
<212> TYPE: PRT
<213> ORGANISM: Homo sapiens

<400> SEQUENCE: 2

Leu Lys Thr Leu Asn Leu Gly Ser Cys Val Ile Ala Thr Asn Leu Gln
 1               5                  10                  15

Glu Ile Arg Asn Gly Phe Ser Asp Ile Arg Gly Ser Val Gln Ala Lys
                20                  25                  30

Asp Gly Asn Ile Asp Ile Arg Ile Leu Arg Arg Thr Glu Ser Leu Gln
            35                  40                  45

Asp Thr Lys Pro Ala Asn Arg Cys Cys Leu Leu Arg His Leu Leu Arg
 50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                    85                  90                  95

Lys Asp Leu Arg Leu Cys His Ala His Met Thr Cys His Cys Gly Glu
                100                 105                 110

Glu Ala Met Lys Lys Tyr Ser Gln Ile Leu Ser His Phe Glu Lys Leu
            115                 120                 125

Glu Pro Gln Ala Ala Val Val Lys Ala Leu Gly Glu Leu Asp Ile Leu
130                 135                 140

Leu Gln Trp Met Glu Glu Thr Glu
145                 150

<210> SEQ ID NO 3
<211> LENGTH: 151
<212> TYPE: PRT
<213> ORGANISM: Homo sapiens

<400> SEQUENCE: 3

Met Lys Ala Ser Ser Leu Ala Phe Ser Leu Leu Ser Ala Ala Phe Tyr
 1               5                  10                  15

Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Asp
            35                  40                  45
```

Ile Arg Gly Ser Val Gln Ala Lys Asp Gly Asn Ile Asp Ile Arg Ile
        50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                     85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys Leu Glu
                115                 120                 125

Pro Gln Ala Ala Val Val Lys Ala Leu Gly Glu Leu Asp Ile Leu Leu
        130                 135                 140

Gln Trp Met Glu Glu Thr Glu
145                 150

<210> SEQ ID NO 4
<211> LENGTH: 127
<212> TYPE: PRT
<213> ORGANISM: Homo sapiens

<400> SEQUENCE: 4

Leu Lys Thr Leu Asn Leu Gly Ser Cys Val Ile Ala Thr Asn Leu Gln
 1               5                  10                  15

Glu Ile Arg Asn Gly Phe Ser Asp Ile Arg Gly Ser Val Gln Ala Lys
                 20                  25                  30

Asp Gly Asn Ile Asp Ile Arg Ile Leu Arg Arg Thr Glu Ser Leu Gln
             35                  40                  45

Asp Thr Lys Pro Ala Asn Arg Cys Cys Leu Leu Arg His Leu Leu Arg
 50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                     85                  90                  95

Lys Asp Leu Arg Leu Cys Leu Glu Pro Gln Ala Ala Val Val Lys Ala
                100                 105                 110

Leu Gly Glu Leu Asp Ile Leu Leu Gln Trp Met Glu Glu Thr Glu
            115                 120                 125

<210> SEQ ID NO 5
<211> LENGTH: 176
<212> TYPE: PRT
<213> ORGANISM: mouse

<400> SEQUENCE: 5

Met Lys Gly Phe Gly Leu Ala Phe Gly Leu Phe Ser Ala Val Gly Phe
 1               5                  10                  15

Leu Leu Trp Thr Pro Leu Thr Gly Leu Lys Thr Leu His Leu Gly Ser
                 20                  25                  30

Cys Val Ile Thr Ala Asn Leu Gln Ala Ile Gln Lys Glu Phe Ser Glu
             35                  40                  45

Ile Arg Asp Ser Val Gln Ala Glu Asp Thr Asn Ile Asp Ile Arg Ile
 50                  55                  60

Leu Arg Thr Thr Glu Ser Leu Lys Asp Ile Lys Ser Leu Asp Arg Cys
 65                  70                  75                  80

Cys Phe Leu Arg His Leu Val Arg Phe Tyr Leu Asp Arg Val Phe Lys
                     85                  90                  95

```
Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
            115                 120                 125

His Met Ala Cys His Cys Gly Glu Glu Ala Met Glu Lys Tyr Asn Gln
        130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175

<210> SEQ ID NO 6
<211> LENGTH: 152
<212> TYPE: PRT
<213> ORGANISM: Mouse

<400> SEQUENCE: 6

Leu Lys Thr Leu His Leu Gly Ser Cys Val Ile Thr Ala Asn Leu Gln
1               5                   10                  15

Ala Ile Gln Lys Glu Phe Ser Glu Ile Arg Asp Ser Val Gln Ala Glu
            20                  25                  30

Asp Thr Asn Ile Asp Ile Arg Ile Leu Arg Thr Thr Glu Ser Leu Lys
        35                  40                  45

Asp Ile Lys Ser Leu Asp Arg Cys Cys Phe Leu Arg His Leu Val Arg
    50                  55                  60

Phe Tyr Leu Asp Arg Val Phe Lys Val Tyr Gln Thr Pro Asp His His
65                  70                  75                  80

Thr Leu Arg Lys Ile Ser Ser Leu Ala Asn Ser Phe Leu Ile Ile Lys
                85                  90                  95

Lys Asp Leu Ser Val Cys His Ser His Met Ala Cys His Cys Gly Glu
            100                 105                 110

Glu Ala Met Glu Lys Tyr Asn Gln Ile Leu Ser His Phe Ile Glu Leu
        115                 120                 125

Glu Leu Gln Ala Ala Val Val Lys Ala Leu Gly Glu Leu Gly Ile Leu
    130                 135                 140

Leu Arg Trp Met Glu Glu Met Leu
145                 150

<210> SEQ ID NO 7
<211> LENGTH: 144
<212> TYPE: PRT
<213> ORGANISM: Mouse

<400> SEQUENCE: 7

Cys Val Ile Thr Ala Asn Leu Gln Ala Ile Gln Lys Glu Phe Ser Glu
1               5                   10                  15

Ile Arg Asp Ser Val Gln Ala Glu Asp Thr Asn Ile Asp Ile Arg Ile
            20                  25                  30

Leu Arg Thr Thr Glu Ser Leu Lys Asp Ile Lys Ser Leu Asp Arg Cys
        35                  40                  45

Cys Phe Leu Arg His Leu Val Arg Phe Tyr Leu Asp Arg Val Phe Lys
    50                  55                  60

Val Tyr Gln Thr Pro Asp His His Thr Leu Arg Lys Ile Ser Ser Leu
65                  70                  75                  80

Ala Asn Ser Phe Leu Ile Ile Lys Lys Asp Leu Ser Val Cys His Ser
                85                  90                  95
```

His Met Ala Cys His Cys Gly Glu Glu Ala Met Glu Lys Tyr Asn Gln
                100                 105                 110

Ile Leu Ser His Phe Ile Glu Leu Glu Leu Gln Ala Ala Val Val Lys
            115                 120                 125

Ala Leu Gly Glu Leu Gly Ile Leu Leu Arg Trp Met Glu Met Leu
    130                 135                 140

<210> SEQ ID NO 8
<211> LENGTH: 154
<212> TYPE: PRT
<213> ORGANISM: Homo sapiens

<400> SEQUENCE: 8

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
            20                  25                  30

Cys Val Ile Thr Ala Asn Leu Gln Ala Ile Gln Lys Glu Phe Ser Glu
        35                  40                  45

Ile Arg Asp Ser Val Ser Leu Asp Arg Cys Cys Phe Leu Arg His Leu
    50                  55                  60

Val Arg Phe Tyr Leu Asp Arg Val Phe Lys Val Tyr Gln Thr Pro Asp
65                  70                  75                  80

His His Thr Leu Arg Lys Ile Ser Ser Leu Ala Asn Ser Phe Leu Ile
                85                  90                  95

Ile Lys Lys Asp Leu Ser Val Cys His Ser His Met Ala Cys His Cys
            100                 105                 110

Gly Glu Glu Ala Met Glu Lys Tyr Asn Gln Ile Leu Ser His Phe Ile
        115                 120                 125

Glu Leu Glu Leu Gln Ala Ala Val Val Lys Ala Leu Gly Glu Leu Gly
    130                 135                 140

Ile Leu Leu Arg Trp Met Glu Met Leu
145                 150

<210> SEQ ID NO 9
<211> LENGTH: 130
<212> TYPE: PRT
<213> ORGANISM: Human

<400> SEQUENCE: 9

Leu Lys Thr Leu His Leu Gly Ser Cys Val Ile Thr Ala Asn Leu Gln
1               5                   10                  15

Ala Ile Gln Lys Glu Phe Ser Glu Ile Arg Asp Ser Val Ser Leu Asp
            20                  25                  30

Arg Cys Cys Phe Leu Arg His Leu Val Arg Phe Tyr Leu Asp Arg Val
        35                  40                  45

Phe Lys Val Tyr Gln Thr Pro Asp His His Thr Leu Arg Lys Ile Ser
    50                  55                  60

Ser Leu Ala Asn Ser Phe Leu Ile Ile Lys Lys Asp Leu Ser Val Cys
65                  70                  75                  80

His Ser His Met Ala Cys His Cys Gly Glu Glu Ala Met Glu Lys Tyr
                85                  90                  95

Asn Gln Ile Leu Ser His Phe Ile Glu Leu Glu Leu Gln Ala Ala Val
            100                 105                 110

Val Lys Ala Leu Gly Glu Leu Gly Ile Leu Leu Arg Trp Met Glu Glu
        115                 120                 125

-continued

```
Met Leu
    130

<210> SEQ ID NO 10
<211> LENGTH: 2831
<212> TYPE: DNA
<213> ORGANISM: human
<220> FEATURE:
<221> NAME/KEY: CDS
<222> LOCATION: (34)...(1755)

<400> SEQUENCE: 10
tagaggccaa gggagggctc tgtgccagcc ccg atg agg acg ctg ctg acc atc        54
                                    Met Arg Thr Leu Leu Thr Ile
                                      1               5 ttg act gtg gga tcc ctg gct gct cac gcc cct gag gac ccc tcg gat        102
Leu Thr Val Gly Ser Leu Ala Ala His Ala Pro Glu Asp Pro Ser Asp
         10                  15                  20 ctg ctc cag cac gtg aaa ttc cag tcc agc aac ttt gaa aac atc ctg        150
Leu Leu Gln His Val Lys Phe Gln Ser Ser Asn Phe Glu Asn Ile Leu
 25                  30                  35 acg tgg gac agc ggg cca gag ggc acc cca gac acg gtc tac agc atc        198
Thr Trp Asp Ser Gly Pro Glu Gly Thr Pro Asp Thr Val Tyr Ser Ile
 40                  45                  50                  55 gag tat aag acg tac gga gag agg gac tgg gtg gca aag aag ggc tgt        246
Glu Tyr Lys Thr Tyr Gly Glu Arg Asp Trp Val Ala Lys Lys Gly Cys
                 60                  65                  70 cag cgg atc acc cgg aag tcc tgc aac ctg acg gtg gag acg ggc aac        294
Gln Arg Ile Thr Arg Lys Ser Cys Asn Leu Thr Val Glu Thr Gly Asn
             75                  80                  85 ctc acg gag ctc tac tat gcc agg gtc acc gct gtc agt gcg gga ggc        342
Leu Thr Glu Leu Tyr Tyr Ala Arg Val Thr Ala Val Ser Ala Gly Gly
         90                  95                 100 cgg tca gcc acc aag atg act gac agg ttc agc tct ctg cag cac act        390
Arg Ser Ala Thr Lys Met Thr Asp Arg Phe Ser Ser Leu Gln His Thr
    105                 110                 115 acc ctc aag cca cct gat gtg acc tgt atc tcc aaa gtg aga tcg att        438
Thr Leu Lys Pro Pro Asp Val Thr Cys Ile Ser Lys Val Arg Ser Ile
120                 125                 130                 135 cag atg att gtt cat cct acc ccc acg cca atc cgt gca ggc gat ggc        486
Gln Met Ile Val His Pro Thr Pro Thr Pro Ile Arg Ala Gly Asp Gly
                140                 145                 150 cac cgg cta acc ctg gaa gac atc ttc cat gac ctg ttc tac cac tta        534
His Arg Leu Thr Leu Glu Asp Ile Phe His Asp Leu Phe Tyr His Leu
            155                 160                 165 gag ctc cag gtc aac cgc acc tac caa atg cac ctt gga ggg aag cag        582
Glu Leu Gln Val Asn Arg Thr Tyr Gln Met His Leu Gly Gly Lys Gln
        170                 175                 180 aga gaa tat gag ttc ttc ggc ctg acc cct gac aca gag ttc ctt ggc        630
Arg Glu Tyr Glu Phe Phe Gly Leu Thr Pro Asp Thr Glu Phe Leu Gly
    185                 190                 195 acc atc atg att tgc gtt ccc acc tgg gcc aag gag agt gcc ccc tac        678
Thr Ile Met Ile Cys Val Pro Thr Trp Ala Lys Glu Ser Ala Pro Tyr
200                 205                 210                 215 atg tgc cga gtg aag aca ctg cca gac cgg aca tgg acc tac tcc ttc        726
Met Cys Arg Val Lys Thr Leu Pro Asp Arg Thr Trp Thr Tyr Ser Phe
                220                 225                 230 tcc gga gcc ttc ctg ttc tcc atg ggc ttc ctc gtc gca gta ctc tgc        774
Ser Gly Ala Phe Leu Phe Ser Met Gly Phe Leu Val Ala Val Leu Cys
            235                 240                 245 tac ctg agc tac aga tat gtc acc aag ccg cct gca cct ccc aac tcc        822
```

```
                    -continued

Tyr Leu Ser Tyr Arg Tyr Val Thr Lys Pro Pro Ala Pro Pro Asn Ser
        250             255             260 ctg aac gtc cag cga gtc ctg act ttc cag ccg ctg cgc ttc atc cag      870
Leu Asn Val Gln Arg Val Leu Thr Phe Gln Pro Leu Arg Phe Ile Gln
    265             270             275 gag cac gtc ctg atc cct gtc ttt gac ctc agc ggc ccc agc agt ctg      918
Glu His Val Leu Ile Pro Val Phe Asp Leu Ser Gly Pro Ser Ser Leu
280             285             290             295 gcc cag cct gtc cag tac tcc cag atc agg gtg tct gga ccc agg gag      966
Ala Gln Pro Val Gln Tyr Ser Gln Ile Arg Val Ser Gly Pro Arg Glu
            300             305             310 ccc gca gga gct cca cag cgg cat agc ctg tcc gag atc acc tac tta     1014
Pro Ala Gly Ala Pro Gln Arg His Ser Leu Ser Glu Ile Thr Tyr Leu
        315             320             325 ggg cag cca gac atc tcc atc ctc cag ccc tcc aac gtg cca cct ccc     1062
Gly Gln Pro Asp Ile Ser Ile Leu Gln Pro Ser Asn Val Pro Pro Pro
            330             335             340 cag atc ctc tcc cca ctg tcc tat gcc cca aac gct gcc cct gag gtc     1110
Gln Ile Leu Ser Pro Leu Ser Tyr Ala Pro Asn Ala Ala Pro Glu Val
        345             350             355 ggg ccc cca tcc tat gca cct cag gtg acc ccc gaa gct caa ttc cca     1158
Gly Pro Pro Ser Tyr Ala Pro Gln Val Thr Pro Glu Ala Gln Phe Pro
360             365             370             375 ttc tac gcc cca cag gcc atc tct aag gtc cag cct tcc tcc tat gcc     1206
Phe Tyr Ala Pro Gln Ala Ile Ser Lys Val Gln Pro Ser Ser Tyr Ala
            380             385             390 cct caa gcc act ccg gac agc tgg cct ccc tcc tat ggg gta tgc atg     1254
Pro Gln Ala Thr Pro Asp Ser Trp Pro Pro Ser Tyr Gly Val Cys Met
        395             400             405 gaa ggt tct ggc aaa gac tcc ccc act ggg aca ctt tct agt cct aaa     1302
Glu Gly Ser Gly Lys Asp Ser Pro Thr Gly Thr Leu Ser Ser Pro Lys
            410             415             420 cac ctt agg cct aaa ggt cag ctt cag aaa gag cca cca gct gga agc     1350
His Leu Arg Pro Lys Gly Gln Leu Gln Lys Glu Pro Pro Ala Gly Ser
425             430             435 tgc atg tta ggt ggc ctt tct ctg cag gag gtg acc tcc ttg gct atg     1398
Cys Met Leu Gly Gly Leu Ser Leu Gln Glu Val Thr Ser Leu Ala Met
440             445             450             455 gag gaa tcc caa gaa gca aaa tca ttg cac cag ccc ctg ggg att tgc     1446
Glu Glu Ser Gln Glu Ala Lys Ser Leu His Gln Pro Leu Gly Ile Cys
            460             465             470 aca gac aga aca tct gac cca aat gtg cta cac agt ggg gag gaa ggg     1494
Thr Asp Arg Thr Ser Asp Pro Asn Val Leu His Ser Gly Glu Glu Gly
        475             480             485 aca cca cag tac cta aag ggc cag ctc ccc ctc ctc tca tca gtc cag     1542
Thr Pro Gln Tyr Leu Lys Gly Gln Leu Pro Leu Leu Ser Ser Val Gln
        490             495             500 atc gag ggc cac ccc atg tcc ctc cct ttg caa cct cct tcc ggt cca     1590
Ile Glu Gly His Pro Met Ser Leu Pro Leu Gln Pro Pro Ser Gly Pro
        505             510             515 tgt tcc ccc tcg gac caa ggt cca agt ccc tgg ggc ctg ctg gag tcc     1638
Cys Ser Pro Ser Asp Gln Gly Pro Ser Pro Trp Gly Leu Leu Glu Ser
520             525             530             535 ctt gtg tgt ccc aag gat gaa gcc aag agc cca gcc cct gag acc tca     1686
Leu Val Cys Pro Lys Asp Glu Ala Lys Ser Pro Ala Pro Glu Thr Ser
            540             545             550 gac ctg gag cag ccc aca gaa ctg gat tct ctt ttc aga ggc ctg gcc     1734
Asp Leu Glu Gln Pro Thr Glu Leu Asp Ser Leu Phe Arg Gly Leu Ala
        555             560             565
```

-continued

```
ctg act gtg cag tgg gag tcc tgaggggaat gggaaaggct tggtgcttcc      1785
Leu Thr Val Gln Trp Glu Ser
        570 tccctgtccc tacccagtgt cacatccttg gctgtcaatc ccatgcctgc ccatgccaca   1845 cactctgcga tctggcctca gacgggtgcc cttgagagaa gcagagggag tggcatgcag   1905 ggcccctgcc atgggtgcgc tcctcaccgg aacaaagcag catgataagg actgcagcgg   1965 gggagctctg gggagcagct tgtgtagaca agcgcgtgct cgctgagccc tgcaaggcag   2025 aaatgacagt gcaaggagga aatgcaggga actcccgag gtccagagcc ccacctccta    2085 acaccatgga ttcaaagtgc tcagggaatt tgcctctcct tgccccattc ctggccagtt   2145 tcacaatcta gctcgacaga gcatgaggcc cctgcctctt ctgtcattgt tcaaaggtgg   2205 gaagagagcc tggaaaagaa ccaggcctgg aaaagaacca aaggaggct gggcagaacc     2265 agaacaacct gcacttctgc caaggccagg ccagcagga cggcaggact ctagggaggg    2325 gtgtggcctg cagctcattc ccagccaggg caactgcctg acgttgcacg atttcagctt   2385 cattcctctg atagaacaaa gcgaaatgca ggtccaccag ggagggagac acacaagcct   2445 tttctgcagg caggagtttc agaccctatc ctgagaatgg ggtttgaaag gaaggtgagg   2505 gctgtggccc ctggacgggt acaataacac actgtactga tgtcacaact ttgcaagctc   2565 tgccttgggt tcagcccatc tgggctcaaa ttccagcctc accactcaca agctgtgtga   2625 cttcaaacaa atgaaatcag tgcccagaac ctcggtttcc tcatctgtaa tgtggggatc   2685 ataaccccta cctcatggag ttgtggtgaa gatgaaatga agtcatgtct ttaaagtgct   2745 taatagtgcc tggtacatgg gcagtgccca ataaacggta gctatttaaa aaaaaaaaa    2805 aaaaaaaaaa atagcggccg cctcga                                       2831
```

<210> SEQ ID NO 11
<211> LENGTH: 574
<212> TYPE: PRT
<213> ORGANISM: human

<400> SEQUENCE: 11

```
Met Arg Thr Leu Leu Thr Ile Leu Thr Val Gly Ser Leu Ala Ala His
  1               5                  10                  15

Ala Pro Glu Asp Pro Ser Asp Leu Leu Gln His Val Lys Phe Gln Ser
             20                  25                  30

Ser Asn Phe Glu Asn Ile Leu Thr Trp Asp Ser Gly Pro Glu Gly Thr
         35                  40                  45

Pro Asp Thr Val Tyr Ser Ile Glu Tyr Lys Thr Tyr Gly Glu Arg Asp
     50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
```

-continued

```
                165                 170                 175
Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
        515                 520                 525

Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570
```

<210> SEQ ID NO 12

<211> LENGTH: 228
<212> TYPE: PRT
<213> ORGANISM: human

<400> SEQUENCE: 12

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr
225

<210> SEQ ID NO 13
<211> LENGTH: 211
<212> TYPE: PRT
<213> ORGANISM: human

<400> SEQUENCE: 13

Pro Glu Asp Pro Ser Asp Leu Leu Gln His Val Lys Phe Gln Ser Ser
1               5                   10                  15

Asn Phe Glu Asn Ile Leu Thr Trp Asp Ser Gly Pro Glu Gly Thr Pro
            20                  25                  30

Asp Thr Val Tyr Ser Ile Glu Tyr Lys Thr Tyr Gly Glu Arg Asp Trp
        35                  40                  45

Val Ala Lys Lys Gly Cys Gln Arg Ile Thr Arg Lys Ser Cys Asn Leu
    50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met Thr Asp Arg Phe
                85                  90                  95

Ser Ser Leu Gln His Thr Thr Leu Lys Pro Pro Asp Val Thr Cys Ile
            100                 105                 110

```
Ser Lys Val Arg Ser Ile Gln Met Ile Val His Pro Thr Pro Thr Pro
        115                 120                 125

Ile Arg Ala Gly Asp Gly His Arg Leu Thr Leu Glu Asp Ile Phe His
    130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175

Asp Thr Glu Phe Leu Gly Thr Ile Met Ile Cys Val Pro Thr Trp Ala
            180                 185                 190

Lys Glu Ser Ala Pro Tyr Met Cys Arg Val Lys Thr Leu Pro Asp Arg
        195                 200                 205

Thr Trp Thr
    210

<210> SEQ ID NO 14
<211> LENGTH: 971
<212> TYPE: DNA
<213> ORGANISM: Human
<220> FEATURE:
<221> NAME/KEY: CDS
<222> LOCATION: (18)...(950)

<400> SEQUENCE: 14
gaattcgagt ctaccaa atg cag act ttc aca atg gtt cta gaa gaa atc         50
                   Met Gln Thr Phe Thr Met Val Leu Glu Glu Ile
                    1               5                   10 tgg aca agt ctt ttc atg tgg ttt ttc tac gca ttg att cca tgt ttg         98
Trp Thr Ser Leu Phe Met Trp Phe Phe Tyr Ala Leu Ile Pro Cys Leu
         15                  20                  25 ctc aca gat gaa gtg gcc att ctg cct gcc cct cag aac ctc tct gta       146
Leu Thr Asp Glu Val Ala Ile Leu Pro Ala Pro Gln Asn Leu Ser Val
             30                  35                  40 ctc tca acc aac atg aag cat ctc ttg atg tgg agc cca gtg atc gcg       194
Leu Ser Thr Asn Met Lys His Leu Leu Met Trp Ser Pro Val Ile Ala
     45                  50                  55 cct gga gaa aca gtg tac tat tct gtc gaa tac cag ggg gag tac gag       242
Pro Gly Glu Thr Val Tyr Tyr Ser Val Glu Tyr Gln Gly Glu Tyr Glu
 60                  65                  70                  75 agc ctg tac acg agc cac atc tgg atc ccc agc agc tgg tgc tca ctc       290
Ser Leu Tyr Thr Ser His Ile Trp Ile Pro Ser Ser Trp Cys Ser Leu
                 80                  85                  90 act gaa ggt cct gag tgt gat gtc act gat gac atc acg gcc act gtg       338
Thr Glu Gly Pro Glu Cys Asp Val Thr Asp Asp Ile Thr Ala Thr Val
             95                 100                 105 cca tac aac ctt cgt gtc agg gcc aca ttg ggc tca cag acc tca gcc       386
Pro Tyr Asn Leu Arg Val Arg Ala Thr Leu Gly Ser Gln Thr Ser Ala
         110                 115                 120 tgg agc atc ctg aag cat ccc ttt aat aga aac tca acc atc ctt acc       434
Trp Ser Ile Leu Lys His Pro Phe Asn Arg Asn Ser Thr Ile Leu Thr
     125                 130                 135 cga cct ggg atg gag atc acc aaa gat ggc ttc cac ctg gtt att gag       482
Arg Pro Gly Met Glu Ile Thr Lys Asp Gly Phe His Leu Val Ile Glu
140                 145                 150                 155 ctg gag gac ctg ggg ccc cag ttt gag ttc ctt gtg gcc tac tgg agg       530
Leu Glu Asp Leu Gly Pro Gln Phe Glu Phe Leu Val Ala Tyr Trp Arg
                 160                 165                 170 agg gag cct ggt gcc gag gaa cat gtc aaa atg gtg agg agt ggg ggt       578
Arg Glu Pro Gly Ala Glu Glu His Val Lys Met Val Arg Ser Gly Gly
```

-continued

|  |  | 175 |  |  |  | 180 |  |  |  | 185 |  |  |  |
|---|---|---|---|---|---|---|---|---|---|---|---|---|---|
| att | cca | gtg | cac | cta | gaa | acc | atg | gag | cca | ggg | gct | gca | tac tgt gtg | 626 |
| Ile | Pro | Val | His | Leu | Glu | Thr | Met | Glu | Pro | Gly | Ala | Ala | Tyr Cys Val |
|  |  | 190 |  |  |  | 195 |  |  |  | 200 |  |  |  |

| aag | gcc | cag | aca | ttc | gtg | aag | gcc | att | ggg | agg | tac | agc | gcc ttc agc | 674 |
| Lys | Ala | Gln | Thr | Phe | Val | Lys | Ala | Ile | Gly | Arg | Tyr | Ser | Ala Phe Ser |
|  | 205 |  |  |  |  | 210 |  |  |  |  | 215 |  |  |

| cag | aca | gaa | tgt | gtg | gag | gtg | caa | gga | gag | gcc | att | ccc | ctg gta ctg | 722 |
| Gln | Thr | Glu | Cys | Val | Glu | Val | Gln | Gly | Glu | Ala | Ile | Pro | Leu Val Leu |
| 220 |  |  |  |  | 225 |  |  |  |  | 230 |  |  | 235 |

| gcc | ctg | ttt | gcc | ttt | gtt | ggc | ttc | atg | ctg | atc | ctt | gtg | gtc gtg cca | 770 |
| Ala | Leu | Phe | Ala | Phe | Val | Gly | Phe | Met | Leu | Ile | Leu | Val | Val Val Pro |
|  |  |  | 240 |  |  |  |  | 245 |  |  |  |  | 250 |

| ctg | ttc | gtc | tgg | aaa | atg | ggc | cgg | ctg | ctc | cag | tac | tcc | tgt tgc ccc | 818 |
| Leu | Phe | Val | Trp | Lys | Met | Gly | Arg | Leu | Leu | Gln | Tyr | Ser | Cys Cys Pro |
|  |  | 255 |  |  |  |  | 260 |  |  |  |  | 265 |  |

| gtg | gtg | gtc | ctc | cca | gac | acc | ttg | aaa | ata | acc | aat | tca | ccc cag aag | 866 |
| Val | Val | Val | Leu | Pro | Asp | Thr | Leu | Lys | Ile | Thr | Asn | Ser | Pro Gln Lys |
|  |  |  | 270 |  |  |  |  | 275 |  |  |  |  | 280 |

| tta | atc | agc | tgc | aga | agg | gag | gag | gtg | gat | gcc | tgt | gcc | acg gct gtg | 914 |
| Leu | Ile | Ser | Cys | Arg | Arg | Glu | Glu | Val | Asp | Ala | Cys | Ala | Thr Ala Val |
|  | 285 |  |  |  |  | 290 |  |  |  |  | 295 |  |  |

| atg | tct | cct | gag | gaa | ctc | ctc | agg | gcc | tgg | atc | tca | taggtttgcg | 960 |
| Met | Ser | Pro | Glu | Glu | Leu | Leu | Arg | Ala | Trp | Ile | Ser |  |
| 300 |  |  |  |  | 305 |  |  |  |  | 310 |  |  |

| gaaggctcga g | 971 |

<210> SEQ ID NO 15
<211> LENGTH: 311
<212> TYPE: PRT
<213> ORGANISM: Human

<400> SEQUENCE: 15

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

```
Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Val Leu Pro
            260                 265                 270

Asp Thr Leu Lys Ile Thr Asn Ser Pro Gln Lys Leu Ile Ser Cys Arg
        275                 280                 285

Arg Glu Glu Val Asp Ala Cys Ala Thr Ala Val Met Ser Pro Glu Glu
    290                 295                 300

Leu Leu Arg Ala Trp Ile Ser
305                 310

<210> SEQ ID NO 16
<211> LENGTH: 203
<212> TYPE: PRT
<213> ORGANISM: human

<400> SEQUENCE: 16

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
        195                 200

<210> SEQ ID NO 17
<211> LENGTH: 201
<212> TYPE: PRT
<213> ORGANISM: Homo sapiens

<400> SEQUENCE: 17
```

```
Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
                100                 105                 110

Gly Met Glu Ile Thr Lys Asp Gly Phe His Leu Val Ile Glu Leu Glu
            115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
        195                 200

<210> SEQ ID NO 18
<211> LENGTH: 201
<212> TYPE: PRT
<213> ORGANISM: Homo sapiens

<400> SEQUENCE: 18

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
                100                 105                 110

Gly Met Glu Ile Pro Lys His Gly Phe His Leu Val Ile Glu Leu Glu
            115                 120                 125

Asp Leu Gly Pro Gln Phe Glu Phe Leu Val Ala Tyr Trp Thr Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
```

```
              165                 170                 175
Gln Thr Phe Val Lys Ala Ile Gly Arg Tyr Ser Ala Phe Ser Gln Thr
        180                 185                 190

Glu Cys Val Glu Val Gln Gly Glu Ala
        195                 200

<210> SEQ ID NO 19
<211> LENGTH: 196
<212> TYPE: PRT
<213> ORGANISM: Homo sapiens

<400> SEQUENCE: 19

Leu Pro Ala Pro Gln Asn Leu Ser Val Leu Ser Thr Asn Met Lys His
  1               5                  10                  15

Leu Leu Met Trp Ser Pro Val Ile Ala Pro Gly Glu Thr Val Tyr Tyr
             20                  25                  30

Ser Val Glu Tyr Gln Gly Glu Tyr Glu Ser Leu Tyr Thr Ser His Ile
         35                  40                  45

Trp Ile Pro Ser Ser Trp Cys Ser Leu Thr Glu Gly Pro Glu Cys Asp
 50                  55                  60

Val Thr Asp Asp Ile Thr Ala Thr Val Pro Tyr Asn Leu Arg Val Arg
 65                  70                  75                  80

Ala Thr Leu Gly Ser Gln Thr Ser Ala Trp Ser Ile Leu Lys His Pro
                 85                  90                  95

Phe Asn Arg Asn Ser Thr Ile Leu Thr Arg Pro Gly Met Glu Ile Thr
            100                 105                 110

Lys Asp Gly Phe His Leu Val Ile Glu Leu Glu Asp Leu Gly Pro Gln
        115                 120                 125

Phe Glu Phe Leu Val Ala Tyr Trp Arg Arg Glu Pro Gly Ala Glu Glu
    130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175

Ala Ile Gly Arg Tyr Ser Ala Phe Ser Gln Thr Glu Cys Val Glu Val
            180                 185                 190

Gln Gly Glu Ala
        195

<210> SEQ ID NO 20
<211> LENGTH: 203
<212> TYPE: PRT
<213> ORGANISM: Homo sapiens

<400> SEQUENCE: 20

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
             20                  25                  30

Glu Thr Val Tyr Tyr Ser Val Glu Tyr Gln Gly Glu Tyr Glu Ser Leu
         35                  40                  45

Tyr Thr Ser His Ile Trp Ile Pro Ser Ser Trp Cys Ser Leu Thr Glu
     50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
```

```
                      85                  90                  95
Ile Leu Lys His Pro Phe Asn Arg Asn Ser Thr Ile Leu Thr Arg Pro
                100                 105                 110

Gly Met Glu Ile Pro Lys His Gly Phe His Leu Val Ile Glu Leu Glu
            115                 120                 125

Asp Leu Gly Pro Gln Phe Glu Phe Leu Val Ala Tyr Trp Thr Arg Glu
130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
                180                 185                 190

Glu Cys Val Glu Val Gln Gly Glu Ala Ile Pro
                195                 200

<210> SEQ ID NO 21
<211> LENGTH: 196
<212> TYPE: PRT
<213> ORGANISM: Homo sapiens

<400> SEQUENCE: 21

Leu Pro Ala Pro Gln Asn Leu Ser Val Leu Ser Thr Asn Met Lys His
  1               5                  10                  15

Leu Leu Met Trp Ser Pro Val Ile Ala Pro Gly Glu Thr Val Tyr Tyr
                 20                  25                  30

Ser Val Glu Tyr Gln Gly Glu Tyr Glu Ser Leu Tyr Thr Ser His Ile
                 35                  40                  45

Trp Ile Pro Ser Ser Trp Cys Ser Leu Thr Glu Gly Pro Glu Cys Asp
             50                  55                  60

Val Thr Asp Asp Ile Thr Ala Thr Val Pro Tyr Asn Leu Arg Val Arg
 65                  70                  75                  80

Ala Thr Leu Gly Ser Gln Thr Ser Ala Trp Ser Ile Leu Lys His Pro
                 85                  90                  95

Phe Asn Arg Asn Ser Thr Ile Leu Thr Arg Pro Gly Met Glu Ile Pro
                100                 105                 110

Lys His Gly Phe His Leu Val Ile Glu Leu Glu Asp Leu Gly Pro Gln
            115                 120                 125

Phe Glu Phe Leu Val Ala Tyr Trp Thr Arg Glu Pro Gly Ala Glu Glu
130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175

Ala Ile Gly Arg Tyr Ser Ala Phe Ser Gln Thr Glu Cys Val Glu Val
                180                 185                 190

Gln Gly Glu Ala
        195

<210> SEQ ID NO 22
<211> LENGTH: 1382
<212> TYPE: DNA
<213> ORGANISM: Homo sapiens
<220> FEATURE:
<221> NAME/KEY: CDS
<222> LOCATION: (132)...(1034)
```

<400> SEQUENCE: 22

```
tcgacccacg cgtccgcgct gcgactcaga cctcagctcc aacatatgca ttctgaagaa    60
agatggctga gatggacaga atgctttatt ttggaaagaa acaatgttct aggtcaaact   120
gagtctacca a atg cag act ttc aca atg gtt cta gaa gaa atc tgg aca   170
            Met Gln Thr Phe Thr Met Val Leu Glu Glu Ile Trp Thr
              1               5                  10 agt ctt ttc atg tgg ttt ttc tac gca ttg att cca tgt ttg ctc aca   218
Ser Leu Phe Met Trp Phe Phe Tyr Ala Leu Ile Pro Cys Leu Leu Thr
 15                  20                  25 gat gaa gtg gcc att ctg cct gcc cct cag aac ctc tct gta ctc tca   266
Asp Glu Val Ala Ile Leu Pro Ala Pro Gln Asn Leu Ser Val Leu Ser
 30                  35                  40                  45 acc aac atg aag cat ctc ttg atg tgg agc cca gtg atc gcg cct gga   314
Thr Asn Met Lys His Leu Leu Met Trp Ser Pro Val Ile Ala Pro Gly
                 50                  55                  60 gaa aca gtg tac tat tct gtc gaa tac cag ggg gag tac gag agc ctg   362
Glu Thr Val Tyr Tyr Ser Val Glu Tyr Gln Gly Glu Tyr Glu Ser Leu
                 65                  70                  75 tac acg agc cac atc tgg atc ccc agc agc tgg tgc tca ctc act gaa   410
Tyr Thr Ser His Ile Trp Ile Pro Ser Ser Trp Cys Ser Leu Thr Glu
             80                  85                  90 ggt cct gag tgt gat gtc act gat gac atc acg gcc act gtg cca tac   458
Gly Pro Glu Cys Asp Val Thr Asp Asp Ile Thr Ala Thr Val Pro Tyr
 95                 100                 105 aac ctt cgt gtc agg gcc aca ttg ggc tca cag acc tca gcc tgg agc   506
Asn Leu Arg Val Arg Ala Thr Leu Gly Ser Gln Thr Ser Ala Trp Ser
110                 115                 120                 125 atc ctg aag cat ccc ttt aat aga aac tca acc atc ctt acc cga cct   554
Ile Leu Lys His Pro Phe Asn Arg Asn Ser Thr Ile Leu Thr Arg Pro
                130                 135                 140 ggg atg gag atc ccc aaa cat ggc ttc cac ctg gtt att gag ctg gag   602
Gly Met Glu Ile Pro Lys His Gly Phe His Leu Val Ile Glu Leu Glu
                145                 150                 155 gac ctg ggg ccc cag ttt gag ttc ctt gtg gcc tac tgg acg agg gag   650
Asp Leu Gly Pro Gln Phe Glu Phe Leu Val Ala Tyr Trp Thr Arg Glu
                160                 165                 170 cct ggt gcc gag gaa cat gtc aaa atg gtg agg agt ggg ggt att cca   698
Pro Gly Ala Glu Glu His Val Lys Met Val Arg Ser Gly Gly Ile Pro
175                 180                 185 gtg cac cta gaa acc atg gag cca ggg gct gca tac tgt gtg aag gcc   746
Val His Leu Glu Thr Met Glu Pro Gly Ala Ala Tyr Cys Val Lys Ala
190                 195                 200                 205 cag aca ttc gtg aag gcc att ggg agg tac agc gcc ttc agc cag aca   794
Gln Thr Phe Val Lys Ala Ile Gly Arg Tyr Ser Ala Phe Ser Gln Thr
                210                 215                 220 gaa tgt gtg gag gtg caa gga gag gcc att ccc ctg gta ctg gcc ctg   842
Glu Cys Val Glu Val Gln Gly Glu Ala Ile Pro Leu Val Leu Ala Leu
                225                 230                 235 ttt gcc ttt gtt ggc ttc atg ctg atc ctt gtg gtc gtg cca ctg ttc   890
Phe Ala Phe Val Gly Phe Met Leu Ile Leu Val Val Val Pro Leu Phe
                240                 245                 250 gtc tgg aaa atg ggc cgg ctg ctc cag tac tcc tgt tgc ccc gtg gtg   938
Val Trp Lys Met Gly Arg Leu Leu Gln Tyr Ser Cys Cys Pro Val Val
255                 260                 265 gtc ctc cca gac acc ttg aaa ata acc aat tca ccc cag gtt aat cag   986
Val Leu Pro Asp Thr Leu Lys Ile Thr Asn Ser Pro Gln Val Asn Gln
270                 275                 280                 285 ctg cag aag gga gga ggt gga tgc ctg tgc cac ggc tgt gat gtc tcc  1034
```

```
Leu Gln Lys Gly Gly Gly Gly Cys Leu Cys His Gly Cys Asp Val Ser
            290                 295                 300 tgaggaactc ctcagggcct ggatctcata tcaggtttgc ggaagggccc aggtgaagcc    1094
gagaacctgg tctgcatgac atggaaacca tgagggggaca agttgtgttt ctgttttccg   1154
ccacggacaa gggatgagag aagtaggaag agcctgttgt ctacaagtct agaagcaacc    1214
atcagaggca gggtggtttg tctaacagaa caactgactg aggctatggg ggttgtgacc    1274
tctagacttt gggcttccac ttgcttggct gagcaaccct gggaaaagtg acttcatccc    1334
ttcggtccca agttttctca tctgtaatgg gggatcccta caaaactg                1382

<210> SEQ ID NO 23
<211> LENGTH: 301
<212> TYPE: PRT
<213> ORGANISM: Homo sapiens

<400> SEQUENCE: 23

Met Gln Thr Phe Thr Met Val Leu Glu Glu Ile Trp Thr Ser Leu Phe
  1               5                  10                  15

Met Trp Phe Phe Tyr Ala Leu Ile Pro Cys Leu Leu Thr Asp Glu Val
             20                  25                  30

Ala Ile Leu Pro Ala Pro Gln Asn Leu Ser Val Leu Ser Thr Asn Met
         35                  40                  45

Lys His Leu Leu Met Trp Ser Pro Val Ile Ala Pro Gly Glu Thr Val
     50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                 85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Val Leu Pro
            260                 265                 270

Asp Thr Leu Lys Ile Thr Asn Ser Pro Gln Val Asn Gln Leu Gln Lys
        275                 280                 285

Gly Gly Gly Gly Cys Leu Cys His Gly Cys Asp Val Ser
    290                 295                 300
```

```
<210> SEQ ID NO 24
<211> LENGTH: 1764
<212> TYPE: DNA
<213> ORGANISM: Homo sapiens
<220> FEATURE:
<221> NAME/KEY: CDS
<222> LOCATION: (34)...(1752)

<400> SEQUENCE: 24
```

| | | | | | | | | | | | | | | | | |
|---|---|---|---|---|---|---|---|---|---|---|---|---|---|---|---|---|
| tagaggccaa | gggagggctc | tgtgccagcc | ccg | atg | agg | acg | ctg | ctg | acc | atc | | | | | | 54 |
| | | | | Met | Arg | Thr | Leu | Leu | Thr | Ile | | | | | | |
| | | | | 1 | | | | 5 | | | | | | | | |
| ttg | act | gtg | gga | tcc | ctg | gct | gct | cac | gcc | cct | gag | gac | ccc | tcg | gat | 102 |
| Leu | Thr | Val | Gly | Ser | Leu | Ala | Ala | His | Ala | Pro | Glu | Asp | Pro | Ser | Asp | |
| | 10 | | | | 15 | | | | 20 | | | | | | | |
| ctg | ctc | cag | cac | gtg | aaa | ttc | cag | tcc | agc | aac | ttt | gaa | aac | atc | ctg | 150 |
| Leu | Leu | Gln | His | Val | Lys | Phe | Gln | Ser | Ser | Asn | Phe | Glu | Asn | Ile | Leu | |
| | 25 | | | | 30 | | | | 35 | | | | | | | |
| acg | tgg | gac | agc | ggg | cca | gag | ggc | acc | cca | gac | acg | gtc | tac | agc | atc | 198 |
| Thr | Trp | Asp | Ser | Gly | Pro | Glu | Gly | Thr | Pro | Asp | Thr | Val | Tyr | Ser | Ile | |
| 40 | | | | 45 | | | | 50 | | | | | | | 55 | |
| gag | tat | aag | acg | tac | gga | gag | agg | gac | tgg | gtg | gca | aag | aag | ggc | tgt | 246 |
| Glu | Tyr | Lys | Thr | Tyr | Gly | Glu | Arg | Asp | Trp | Val | Ala | Lys | Lys | Gly | Cys | |
| | | | 60 | | | | | 65 | | | | | 70 | | | |
| cag | cgg | atc | acc | cgg | aag | tcc | tgc | aac | ctg | acg | gtg | gag | acg | ggc | aac | 294 |
| Gln | Arg | Ile | Thr | Arg | Lys | Ser | Cys | Asn | Leu | Thr | Val | Glu | Thr | Gly | Asn | |
| | | 75 | | | | | 80 | | | | | 85 | | | | |
| ctc | acg | gag | ctc | tac | tat | gcc | agg | gtc | acc | gct | gtc | agt | gcg | gga | ggc | 342 |
| Leu | Thr | Glu | Leu | Tyr | Tyr | Ala | Arg | Val | Thr | Ala | Val | Ser | Ala | Gly | Gly | |
| | | 90 | | | | 95 | | | | | 100 | | | | | |
| cgg | tca | gcc | acc | aag | atg | act | gac | agg | ttc | agc | tct | ctg | cag | cac | act | 390 |
| Arg | Ser | Ala | Thr | Lys | Met | Thr | Asp | Arg | Phe | Ser | Ser | Leu | Gln | His | Thr | |
| | 105 | | | | 110 | | | | 115 | | | | | | | |
| acc | ctc | aag | cca | cct | gat | gtg | acc | tgt | atc | tcc | aaa | gtg | aga | tcg | att | 438 |
| Thr | Leu | Lys | Pro | Pro | Asp | Val | Thr | Cys | Ile | Ser | Lys | Val | Arg | Ser | Ile | |
| 120 | | | | 125 | | | | 130 | | | | | | | 135 | |
| cag | atg | att | gtt | cat | cct | acc | ccc | acg | cca | atc | cgt | gca | ggc | gat | ggc | 486 |
| Gln | Met | Ile | Val | His | Pro | Thr | Pro | Thr | Pro | Ile | Arg | Ala | Gly | Asp | Gly | |
| | | | 140 | | | | 145 | | | | | 150 | | | | |
| cac | cgg | cta | acc | ctg | gaa | gac | atc | ttc | cat | gac | ctg | ttc | tac | cac | tta | 534 |
| His | Arg | Leu | Thr | Leu | Glu | Asp | Ile | Phe | His | Asp | Leu | Phe | Tyr | His | Leu | |
| | | 155 | | | | | 160 | | | | | 165 | | | | |
| gag | ctc | cag | gtc | aac | cgc | acc | tac | caa | atg | cac | ctt | gga | ggg | aag | cag | 582 |
| Glu | Leu | Gln | Val | Asn | Arg | Thr | Tyr | Gln | Met | His | Leu | Gly | Gly | Lys | Gln | |
| | | 170 | | | | | 175 | | | | | 180 | | | | |
| aga | gaa | tat | gag | ttc | ttc | ggc | ctg | acc | cct | gac | aca | gag | ttc | ctt | ggc | 630 |
| Arg | Glu | Tyr | Glu | Phe | Phe | Gly | Leu | Thr | Pro | Asp | Thr | Glu | Phe | Leu | Gly | |
| | 185 | | | | 190 | | | | 195 | | | | | | | |
| acc | atc | atg | att | tgc | gtt | ccc | acc | tgg | gcc | aag | gag | agt | gcc | ccc | tac | 678 |
| Thr | Ile | Met | Ile | Cys | Val | Pro | Thr | Trp | Ala | Lys | Glu | Ser | Ala | Pro | Tyr | |
| 200 | | | | 205 | | | | 210 | | | | | | | 215 | |
| atg | tgc | cga | gtg | aag | aca | ctg | cca | gac | cgg | aca | tgg | acc | ggt | gga | ggc | 726 |
| Met | Cys | Arg | Val | Lys | Thr | Leu | Pro | Asp | Arg | Thr | Trp | Thr | Gly | Gly | Gly | |
| | | | 220 | | | | 225 | | | | | 230 | | | | |
| ggt | tca | ggc | gga | ggt | ggc | tct | ggc | ggt | ggc | gga | tcg | gcc | tcc | acc | aag | 774 |
| Gly | Ser | Gly | Gly | Gly | Gly | Ser | Gly | Gly | Gly | Gly | Ser | Ala | Ser | Thr | Lys | |
| | | 235 | | | | | 240 | | | | | 245 | | | | |
| ggc | cca | tcg | gtc | ttc | ccc | ctg | gca | ccc | tcc | tcc | aag | agc | acc | tct | ggg | 822 |
| Gly | Pro | Ser | Val | Phe | Pro | Leu | Ala | Pro | Ser | Ser | Lys | Ser | Thr | Ser | Gly | |
| | 250 | | | | 255 | | | | 260 | | | | | | | |

```
ggc aca gcg gcc ctg ggc tgc ctg gtc aag gac tac ttc ccc gaa ccg        870
Gly Thr Ala Ala Leu Gly Cys Leu Val Lys Asp Tyr Phe Pro Glu Pro
265                 270                 275 gtg acg gtg tcg tgg aac tca ggc gcc ctg acc agc ggc gtg cac acc        918
Val Thr Val Ser Trp Asn Ser Gly Ala Leu Thr Ser Gly Val His Thr
280                 285                 290                 295 ttc ccg gct gtc cta cag tcc tca gga ctc tac tcc ctc agc agc gtg        966
Phe Pro Ala Val Leu Gln Ser Ser Gly Leu Tyr Ser Leu Ser Ser Val
                300                 305                 310 gtg acc gtg ccc tcc agc agc ttg ggc acc cag acc tac atc tgc aac       1014
Val Thr Val Pro Ser Ser Ser Leu Gly Thr Gln Thr Tyr Ile Cys Asn
            315                 320                 325 gtg aat cac aag ccc agc aac acc aag gtg gac aag aaa gtt gag ccc       1062
Val Asn His Lys Pro Ser Asn Thr Lys Val Asp Lys Lys Val Glu Pro
        330                 335                 340 aaa tct tgt gac aaa act cac aca tgc cca ccg tgc cca gca cct gaa       1110
Lys Ser Cys Asp Lys Thr His Thr Cys Pro Pro Cys Pro Ala Pro Glu
345                 350                 355 gcc gag ggg gca ccg tca gtc ttc ctc ttc ccc cca aaa ccc aag gac       1158
Ala Glu Gly Ala Pro Ser Val Phe Leu Phe Pro Pro Lys Pro Lys Asp
360                 365                 370                 375 acc ctc atg atc tcc cgg acc cct gag gtc aca tgc gtg gtg gtg gac       1206
Thr Leu Met Ile Ser Arg Thr Pro Glu Val Thr Cys Val Val Val Asp
                380                 385                 390 gtg agc cac gaa gac cct gag gtc aag ttc aac tgg tac gtg gac ggc       1254
Val Ser His Glu Asp Pro Glu Val Lys Phe Asn Trp Tyr Val Asp Gly
            395                 400                 405 gtg gag gtg cat aat gcc aag aca aag ccg cgg gag gag cag tac aac       1302
Val Glu Val His Asn Ala Lys Thr Lys Pro Arg Glu Glu Gln Tyr Asn
        410                 415                 420 agc acg tac cgt gtg gtc agc gtc ctc acc gtc ctg cac cag gac tgg       1350
Ser Thr Tyr Arg Val Val Ser Val Leu Thr Val Leu His Gln Asp Trp
425                 430                 435 ctg aat ggc aag gag tac aag tgc aag gtc tcc aac aaa gcc ctc cca       1398
Leu Asn Gly Lys Glu Tyr Lys Cys Lys Val Ser Asn Lys Ala Leu Pro
440                 445                 450                 455 tcc tcc atc gag aaa acc atc tcc aaa gcc aaa ggg cag ccc cga gaa       1446
Ser Ser Ile Glu Lys Thr Ile Ser Lys Ala Lys Gly Gln Pro Arg Glu
                460                 465                 470 cca cag gtg tac acc ctg ccc cca tcc cgg gat gag ctg acc aag aac       1494
Pro Gln Val Tyr Thr Leu Pro Pro Ser Arg Asp Glu Leu Thr Lys Asn
            475                 480                 485 cag gtc agc ctg acc tgc ctg gtc aaa ggc ttc tat ccc agc gac atc       1542
Gln Val Ser Leu Thr Cys Leu Val Lys Gly Phe Tyr Pro Ser Asp Ile
        490                 495                 500 gcc gtg gag tgg gag agc aat ggg cag ccg gag aac aac tac aag acc       1590
Ala Val Glu Trp Glu Ser Asn Gly Gln Pro Glu Asn Asn Tyr Lys Thr
505                 510                 515 acg cct ccc gtg ctg gac tcc gac ggc tcc ttc ttc ctc tac agc aag       1638
Thr Pro Pro Val Leu Asp Ser Asp Gly Ser Phe Phe Leu Tyr Ser Lys
520                 525                 530                 535 ctc acc gtg gac aag agc agg tgg cag cag ggg aac gtc ttc tca tgc       1686
Leu Thr Val Asp Lys Ser Arg Trp Gln Gln Gly Asn Val Phe Ser Cys
                540                 545                 550 tcc gtg atg cat gag gct ctg cac aac cac tac acg cag aag agc ctc       1734
Ser Val Met His Glu Ala Leu His Asn His Tyr Thr Gln Lys Ser Leu
555                 560                 565 tcc ctg tct ccg ggt aaa taatctagat ct                                 1764
Ser Leu Ser Pro Gly Lys
```

<210> SEQ ID NO 25
<211> LENGTH: 573
<212> TYPE: PRT
<213> ORGANISM: Homo sapiens

<400> SEQUENCE: 25

```
Met Arg Thr Leu Leu Thr Ile Leu Thr Val Gly Ser Leu Ala Ala His
  1               5                  10                  15

Ala Pro Glu Asp Pro Ser Asp Leu Leu Gln His Val Lys Phe Gln Ser
             20                  25                  30

Ser Asn Phe Glu Asn Ile Leu Thr Trp Asp Ser Gly Pro Glu Gly Thr
         35                  40                  45

Pro Asp Thr Val Tyr Ser Ile Glu Tyr Lys Thr Tyr Gly Glu Arg Asp
 50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Gly Gly Gly Ser Gly Gly Gly Ser Gly Gly Gly Ser Gly
225                 230                 235                 240

Gly Gly Ser Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Glu Pro Lys Ser Cys Asp Lys Thr His Thr Cys
            340                 345                 350

Pro Pro Cys Pro Ala Pro Glu Ala Glu Gly Ala Pro Ser Val Phe Leu
        355                 360                 365
```

```
Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
                435                 440                 445

Val Ser Asn Lys Ala Leu Pro Ser Ser Ile Glu Lys Thr Ile Ser Lys
    450                 455                 460

Ala Lys Gly Gln Pro Arg Glu Pro Gln Val Tyr Thr Leu Pro Pro Ser
465                 470                 475                 480

Arg Asp Glu Leu Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
            515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 26
<211> LENGTH: 556
<212> TYPE: PRT
<213> ORGANISM: Homo sapiens

<400> SEQUENCE: 26

Pro Glu Asp Pro Ser Asp Leu Leu Gln His Val Lys Phe Gln Ser Ser
  1               5                  10                  15

Asn Phe Glu Asn Ile Leu Thr Trp Asp Ser Gly Pro Glu Gly Thr Pro
                 20                  25                  30

Asp Thr Val Tyr Ser Ile Glu Tyr Lys Thr Tyr Gly Glu Arg Asp Trp
             35                  40                  45

Val Ala Lys Lys Gly Cys Gln Arg Ile Thr Arg Lys Ser Cys Asn Leu
     50                  55                  60

Thr Val Glu Thr Gly Asn Leu Thr Glu Leu Tyr Tyr Ala Arg Val Thr
 65                  70                  75                  80

Ala Val Ser Ala Gly Gly Arg Ser Ala Thr Lys Met Thr Asp Arg Phe
                 85                  90                  95

Ser Ser Leu Gln His Thr Thr Leu Lys Pro Pro Asp Val Thr Cys Ile
            100                 105                 110

Ser Lys Val Arg Ser Ile Gln Met Ile Val His Pro Thr Pro Thr Pro
        115                 120                 125

Ile Arg Ala Gly Asp Gly His Arg Leu Thr Leu Glu Asp Ile Phe His
    130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175
```

```
Asp Thr Glu Phe Leu Gly Thr Ile Met Ile Cys Val Pro Thr Trp Ala
            180                 185                 190
Lys Glu Ser Ala Pro Tyr Met Cys Arg Val Lys Thr Leu Pro Asp Arg
        195                 200                 205
Thr Trp Thr Gly Gly Gly Gly Ser Gly Gly Gly Ser Gly Gly Gly
    210                 215                 220
Gly Ser Ala Ser Thr Lys Gly Pro Ser Val Phe Pro Leu Ala Pro Ser
225                 230                 235                 240
Ser Lys Ser Thr Ser Gly Gly Thr Ala Ala Leu Gly Cys Leu Val Lys
            245                 250                 255
Asp Tyr Phe Pro Glu Pro Val Thr Val Ser Trp Asn Ser Gly Ala Leu
        260                 265                 270
Thr Ser Gly Val His Thr Phe Pro Ala Val Leu Gln Ser Ser Gly Leu
    275                 280                 285
Tyr Ser Leu Ser Ser Val Val Thr Val Pro Ser Ser Ser Leu Gly Thr
290                 295                 300
Gln Thr Tyr Ile Cys Asn Val Asn His Lys Pro Ser Asn Thr Lys Val
305                 310                 315                 320
Asp Lys Lys Val Glu Pro Lys Ser Cys Asp Lys Thr His Thr Cys Pro
                325                 330                 335
Pro Cys Pro Ala Pro Glu Ala Glu Gly Ala Pro Ser Val Phe Leu Phe
            340                 345                 350
Pro Pro Lys Pro Lys Asp Thr Leu Met Ile Ser Arg Thr Pro Glu Val
        355                 360                 365
Thr Cys Val Val Val Asp Val Ser His Glu Asp Pro Glu Val Lys Phe
    370                 375                 380
Asn Trp Tyr Val Asp Gly Val Glu Val His Asn Ala Lys Thr Lys Pro
385                 390                 395                 400
Arg Glu Glu Gln Tyr Asn Ser Thr Tyr Arg Val Val Ser Val Leu Thr
                405                 410                 415
Val Leu His Gln Asp Trp Leu Asn Gly Lys Glu Tyr Lys Cys Lys Val
            420                 425                 430
Ser Asn Lys Ala Leu Pro Ser Ser Ile Glu Lys Thr Ile Ser Lys Ala
        435                 440                 445
Lys Gly Gln Pro Arg Glu Pro Gln Val Tyr Thr Leu Pro Pro Ser Arg
    450                 455                 460
Asp Glu Leu Thr Lys Asn Gln Val Ser Leu Thr Cys Leu Val Lys Gly
465                 470                 475                 480
Phe Tyr Pro Ser Asp Ile Ala Val Glu Trp Glu Ser Asn Gly Gln Pro
                485                 490                 495
Glu Asn Asn Tyr Lys Thr Thr Pro Pro Val Leu Asp Ser Asp Gly Ser
            500                 505                 510
Phe Phe Leu Tyr Ser Lys Leu Thr Val Asp Lys Ser Arg Trp Gln Gln
        515                 520                 525
Gly Asn Val Phe Ser Cys Ser Val Met His Glu Ala Leu His Asn His
    530                 535                 540
Tyr Thr Gln Lys Ser Leu Ser Leu Ser Pro Gly Lys
545                 550                 555

<210> SEQ ID NO 27
<211> LENGTH: 1081
<212> TYPE: DNA
<213> ORGANISM: Homo sapiens
<220> FEATURE:
```

<221> NAME/KEY: CDS
<222> LOCATION: (9)...(1067)

<400> SEQUENCE: 27

```
ggccggcc atg cag act ttc aca atg gtt cta gaa gaa atc tgg aca agt         50
         Met Gln Thr Phe Thr Met Val Leu Glu Glu Ile Trp Thr Ser
         1               5                   10 ctt ttc atg tgg ttt ttc tac gca ttg att cca tgt ttg ctc aca gat         98
Leu Phe Met Trp Phe Phe Tyr Ala Leu Ile Pro Cys Leu Leu Thr Asp
15              20                  25                  30 gaa gtg gcc att ctg cct gcc cct cag aac ctc tct gta ctc tca acc         146
Glu Val Ala Ile Leu Pro Ala Pro Gln Asn Leu Ser Val Leu Ser Thr
            35                  40                  45 aac atg aag cat ctc ttg atg tgg agc cca gtg atc gcg cct gga gaa         194
Asn Met Lys His Leu Leu Met Trp Ser Pro Val Ile Ala Pro Gly Glu
        50                  55                  60 aca gtg tac tat tct gtc gaa tac cag ggg gag tac gag agc ctg tac         242
Thr Val Tyr Tyr Ser Val Glu Tyr Gln Gly Glu Tyr Glu Ser Leu Tyr
    65                  70                  75 acg agc cac atc tgg atc ccc agc agc tgg tgc tca ctc act gaa ggt         290
Thr Ser His Ile Trp Ile Pro Ser Ser Trp Cys Ser Leu Thr Glu Gly
80                  85                  90 cct gag tgt gat gtc act gat gac atc acg gcc act gtg cca tac aac         338
Pro Glu Cys Asp Val Thr Asp Asp Ile Thr Ala Thr Val Pro Tyr Asn
95                  100                 105                 110 ctt cgt gtc agg gcc aca ttg ggc tca cag acc tca gcc tgg agc atc         386
Leu Arg Val Arg Ala Thr Leu Gly Ser Gln Thr Ser Ala Trp Ser Ile
            115                 120                 125 ctg aag cat ccc ttt aat aga aac tca acc atc ctt acc cga cct ggg         434
Leu Lys His Pro Phe Asn Arg Asn Ser Thr Ile Leu Thr Arg Pro Gly
        130                 135                 140 atg gag atc ccc aaa cat ggc ttc cac ctg gtt att gag ctg gag gac         482
Met Glu Ile Pro Lys His Gly Phe His Leu Val Ile Glu Leu Glu Asp
    145                 150                 155 ctg ggg ccc cag ttt gag ttc ctt gtg gcc tac tgg acg agg gag cct         530
Leu Gly Pro Gln Phe Glu Phe Leu Val Ala Tyr Trp Thr Arg Glu Pro
160                 165                 170 ggt gcc gag gaa cat gtc aaa atg gtg agg agt ggg ggt att cca gtg         578
Gly Ala Glu Glu His Val Lys Met Val Arg Ser Gly Gly Ile Pro Val
175                 180                 185                 190 cac cta gaa acc atg gag cca ggg gct gca tac tgt gtg aag gcc cag         626
His Leu Glu Thr Met Glu Pro Gly Ala Ala Tyr Cys Val Lys Ala Gln
            195                 200                 205 aca ttc gtg aag gcc att ggg agg tac agc gcc ttc agc cag aca gaa         674
Thr Phe Val Lys Ala Ile Gly Arg Tyr Ser Ala Phe Ser Gln Thr Glu
        210                 215                 220 tgt gtg gag gtg caa gga gag gcc gga ggt ggt ggc agt gga ggc ggc         722
Cys Val Glu Val Gln Gly Glu Ala Gly Gly Gly Gly Ser Gly Gly Gly
    225                 230                 235 ggt agc gga ggc ggt ggc agt cga act gtg gct gca cca tct gtc ttc         770
Gly Ser Gly Gly Gly Gly Ser Arg Thr Val Ala Ala Pro Ser Val Phe
240                 245                 250 atc ttc ccg cca tct gat gag cag ttg aaa tct gga act gcc tct gtt         818
Ile Phe Pro Pro Ser Asp Glu Gln Leu Lys Ser Gly Thr Ala Ser Val
255                 260                 265                 270 gtg tgc ctg ctg aat aac ttc tat ccc aga gag gcc aaa gta cag tgg         866
Val Cys Leu Leu Asn Asn Phe Tyr Pro Arg Glu Ala Lys Val Gln Trp
            275                 280                 285 aag gtg gat aac gcc ctc caa tcg ggt aac tcc cag gag agt gtc aca         914
Lys Val Asp Asn Ala Leu Gln Ser Gly Asn Ser Gln Glu Ser Val Thr
```

-continued

```
                   290                 295                 300
gag cag gac agc aag gac agc acc tac agc ctc agc agc acc ctg acg          962
Glu Gln Asp Ser Lys Asp Ser Thr Tyr Ser Leu Ser Ser Thr Leu Thr
        305                 310                 315 ctg agc aaa gca gac tac gag aaa cac aaa gtc tac gcc tgc gaa gtc         1010
Leu Ser Lys Ala Asp Tyr Glu Lys His Lys Val Tyr Ala Cys Glu Val
320                 325                 330 acc cat cag ggc ctg agc tcg ccc gtc aca aag agc ttc aac agg gga         1058
Thr His Gln Gly Leu Ser Ser Pro Val Thr Lys Ser Phe Asn Arg Gly
335                 340                 345                 350 gag tgt taa tctagaggcg cgcc                                             1081
Glu Cys  *
```

<210> SEQ ID NO 28
<211> LENGTH: 352
<212> TYPE: PRT
<213> ORGANISM: Homo sapiens

<400> SEQUENCE: 28

```
Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
                20                  25                  30

Ala Ile Leu Pro Ala Pro Gln Asn Leu Ser Val Leu Ser Thr Asn Met
            35                  40                  45

Lys His Leu Leu Met Trp Ser Pro Val Ile Ala Pro Gly Glu Thr Val
        50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Gly Gly Gly Ser Gly Gly Gly Gly Ser
225                 230                 235                 240

Gly Gly Gly Gly Ser Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285
```

```
Asp Asn Ala Leu Gln Ser Gly Asn Ser Gln Glu Ser Val Thr Glu Gln
    290                 295                 300
Asp Ser Lys Asp Ser Thr Tyr Ser Leu Ser Ser Thr Leu Thr Leu Ser
305                 310                 315                 320
Lys Ala Asp Tyr Glu Lys His Lys Val Tyr Ala Cys Glu Val Thr His
                325                 330                 335
Gln Gly Leu Ser Ser Pro Val Thr Lys Ser Phe Asn Arg Gly Glu Cys
            340                 345                 350

<210> SEQ ID NO 29
<211> LENGTH: 323
<212> TYPE: PRT
<213> ORGANISM: Homo sapiens

<400> SEQUENCE: 29

Asp Glu Val Ala Ile Leu Pro Ala Pro Gln Asn Leu Ser Val Leu Ser
1               5                   10                  15
Thr Asn Met Lys His Leu Leu Met Trp Ser Pro Val Ile Ala Pro Gly
                20                  25                  30
Glu Thr Val Tyr Tyr Ser Val Glu Tyr Gln Gly Glu Tyr Glu Ser Leu
            35                  40                  45
Tyr Thr Ser His Ile Trp Ile Pro Ser Ser Trp Cys Ser Leu Thr Glu
50                  55                  60
Gly Pro Glu Cys Asp Val Thr Asp Asp Ile Thr Ala Thr Val Pro Tyr
65                  70                  75                  80
Asn Leu Arg Val Arg Ala Thr Leu Gly Ser Gln Thr Ser Ala Trp Ser
                85                  90                  95
Ile Leu Lys His Pro Phe Asn Arg Asn Ser Thr Ile Leu Thr Arg Pro
            100                 105                 110
Gly Met Glu Ile Pro Lys His Gly Phe His Leu Val Ile Glu Leu Glu
        115                 120                 125
Asp Leu Gly Pro Gln Phe Glu Phe Leu Val Ala Tyr Trp Thr Arg Glu
130                 135                 140
Pro Gly Ala Glu Glu His Val Lys Met Val Arg Ser Gly Gly Ile Pro
145                 150                 155                 160
Val His Leu Glu Thr Met Glu Pro Gly Ala Ala Tyr Cys Val Lys Ala
                165                 170                 175
Gln Thr Phe Val Lys Ala Ile Gly Arg Tyr Ser Ala Phe Ser Gln Thr
            180                 185                 190
Glu Cys Val Glu Val Gln Gly Glu Ala Gly Gly Gly Ser Gly Gly
        195                 200                 205
Gly Gly Ser Gly Gly Gly Ser Arg Thr Val Ala Ala Pro Ser Val
    210                 215                 220
Phe Ile Phe Pro Pro Ser Asp Glu Gln Leu Lys Ser Gly Thr Ala Ser
225                 230                 235                 240
Val Val Cys Leu Leu Asn Asn Phe Tyr Pro Arg Glu Ala Lys Val Gln
                245                 250                 255
Trp Lys Val Asp Asn Ala Leu Gln Ser Gly Asn Ser Gln Glu Ser Val
            260                 265                 270
Thr Glu Gln Asp Ser Lys Asp Ser Thr Tyr Ser Leu Ser Ser Thr Leu
        275                 280                 285
Thr Leu Ser Lys Ala Asp Tyr Glu Lys His Lys Val Tyr Ala Cys Glu
    290                 295                 300
Val Thr His Gln Gly Leu Ser Ser Pro Val Thr Lys Ser Phe Asn Arg
305                 310                 315                 320
```

Gly Glu Cys

```
<210> SEQ ID NO 30
<211> LENGTH: 1714
<212> TYPE: DNA
<213> ORGANISM: Homo sapiens
<220> FEATURE:
<221> NAME/KEY: CDS
<222> LOCATION: (34)...(1707)

<400> SEQUENCE: 30
```

| | | |
|---|---|---:|
| tagaggccaa gggagggctc tgtgccagcc ccg atg agg acg ctg ctg acc atc <br>                                                    Met Arg Thr Leu Leu Thr Ile <br>                                                      1               5 | | 54 |
| ttg act gtg gga tcc ctg gct gct cac gcc cct gag gac ccc tcg gat <br> Leu Thr Val Gly Ser Leu Ala Ala His Ala Pro Glu Asp Pro Ser Asp <br>            10                   15                    20 | | 102 |
| ctg ctc cag cac gtg aaa ttc cag tcc agc aac ttt gaa aac atc ctg <br> Leu Leu Gln His Val Lys Phe Gln Ser Ser Asn Phe Glu Asn Ile Leu <br> 25                     30                    35 | | 150 |
| acg tgg gac agc ggg cca gag ggc acc cca gac acg gtc tac agc atc <br> Thr Trp Asp Ser Gly Pro Glu Gly Thr Pro Asp Thr Val Tyr Ser Ile <br> 40                     45                    50                    55 | | 198 |
| gag tat aag acg tac gga gag agg gac tgg gtg gca aag aag ggc tgt <br> Glu Tyr Lys Thr Tyr Gly Glu Arg Asp Trp Val Ala Lys Lys Gly Cys <br>            60                   65                    70 | | 246 |
| cag cgg atc acc cgg aag tcc tgc aac ctg acg gtg gag acg ggc aac <br> Gln Arg Ile Thr Arg Lys Ser Cys Asn Leu Thr Val Glu Thr Gly Asn <br>                    75                    80                    85 | | 294 |
| ctc acg gag ctc tac tat gcc agg gtc acc gct gtc agt gcg gga ggc <br> Leu Thr Glu Leu Tyr Tyr Ala Arg Val Thr Ala Val Ser Ala Gly Gly <br>            90                   95                    100 | | 342 |
| cgg tca gcc acc aag atg act gac agg ttc agc tct ctg cag cac act <br> Arg Ser Ala Thr Lys Met Thr Asp Arg Phe Ser Ser Leu Gln His Thr <br> 105                     110                    115 | | 390 |
| acc ctc aag cca cct gat gtg acc tgt atc tcc aaa gtg aga tcg att <br> Thr Leu Lys Pro Pro Asp Val Thr Cys Ile Ser Lys Val Arg Ser Ile <br> 120                     125                    130                    135 | | 438 |
| cag atg att gtt cat cct acc ccc acg cca atc cgt gca ggc gat ggc <br> Gln Met Ile Val His Pro Thr Pro Thr Pro Ile Arg Ala Gly Asp Gly <br>                    140                    145                    150 | | 486 |
| cac cgg cta acc ctg gaa gac atc ttc cat gac ctg ttc tac cac tta <br> His Arg Leu Thr Leu Glu Asp Ile Phe His Asp Leu Phe Tyr His Leu <br>                       155                    160                    165 | | 534 |
| gag ctc cag gtc aac cgc acc tac caa atg cac ctt gga ggg aag cag <br> Glu Leu Gln Val Asn Arg Thr Tyr Gln Met His Leu Gly Gly Lys Gln <br> 170                     175                    180 | | 582 |
| aga gaa tat gag ttc ttc ggc ctg acc cct gac aca gag ttc ctt ggc <br> Arg Glu Tyr Glu Phe Phe Gly Leu Thr Pro Asp Thr Glu Phe Leu Gly <br> 185                     190                    195 | | 630 |
| acc atc atg att tgc gtt ccc acc tgg gcc aag gag agt gcc ccc tac <br> Thr Ile Met Ile Cys Val Pro Thr Trp Ala Lys Glu Ser Ala Pro Tyr <br> 200                     205                    210                    215 | | 678 |
| atg tgc cga gtg aag aca ctg cca gac cgg aca tgg acc gct agc acc <br> Met Cys Arg Val Lys Thr Leu Pro Asp Arg Thr Trp Thr Ala Ser Thr <br>                    220                    225                    230 | | 726 |
| aag ggc cca tcg gtc ttc ccc ctg gca ccc tcc tcc aag agc acc tct <br> Lys Gly Pro Ser Val Phe Pro Leu Ala Pro Ser Ser Lys Ser Thr Ser <br>                     235                    240                    245 | | 774 |
| ggg ggc aca gcg gcc ctg ggc tgc ctg gtc aag gac tac ttc ccc gaa | | 822 |

|  |  |  |  |  |  |  |  |  |  |  |  |  |
|---|---|---|---|---|---|---|---|---|---|---|---|---|
| Gly | Gly | Thr | Ala | Ala | Leu | Gly | Cys | Leu | Val | Lys | Asp | Tyr | Phe | Pro | Glu |
|  |  | 250 |  |  | 255 |  |  |  |  | 260 |  |  |

```
ccg gtg acg gtg tcg tgg aac tca ggc gcc ctg acc agc ggc gtg cac      870
Pro Val Thr Val Ser Trp Asn Ser Gly Ala Leu Thr Ser Gly Val His
    265                 270                 275 acc ttc ccg gct gtc cta cag tcc tca gga ctc tac tcc ctc agc agc      918
Thr Phe Pro Ala Val Leu Gln Ser Ser Gly Leu Tyr Ser Leu Ser Ser
280                 285                 290                 295 gtg gtg acc gtg ccc tcc agc agc ttg ggc acc cag acc tac atc tgc      966
Val Val Thr Val Pro Ser Ser Ser Leu Gly Thr Gln Thr Tyr Ile Cys
                300                 305                 310 aac gtg aat cac aag ccc agc aac acc aag gtg gac aag aaa gtt gag     1014
Asn Val Asn His Lys Pro Ser Asn Thr Lys Val Asp Lys Lys Val Glu
            315                 320                 325 ccc aaa tct tgt gac aaa act cac aca tgc cca ccg tgc cca gca cct     1062
Pro Lys Ser Cys Asp Lys Thr His Thr Cys Pro Pro Cys Pro Ala Pro
        330                 335                 340 gaa ctc ctg ggg gga ccg tca gtc ttc ctc ttc ccc cca aaa ccc aag     1110
Glu Leu Leu Gly Gly Pro Ser Val Phe Leu Phe Pro Pro Lys Pro Lys
    345                 350                 355 gac acc ctc atg atc tcc cgg acc cct gag gtc aca tgc gtg gtg gtg     1158
Asp Thr Leu Met Ile Ser Arg Thr Pro Glu Val Thr Cys Val Val Val
360                 365                 370                 375 gac gtg agc cac gaa gac cct gag gtc aag ttc aac tgg tac gtg gac     1206
Asp Val Ser His Glu Asp Pro Glu Val Lys Phe Asn Trp Tyr Val Asp
                380                 385                 390 ggc gtg gag gtg cat aat gcc aag aca aag ccg cgg gag gag cag tac     1254
Gly Val Glu Val His Asn Ala Lys Thr Lys Pro Arg Glu Glu Gln Tyr
            395                 400                 405 aac agc acg tac cgt gtg gtc agc gtc ctc acc gtc ctg cac cag gac     1302
Asn Ser Thr Tyr Arg Val Val Ser Val Leu Thr Val Leu His Gln Asp
        410                 415                 420 tgg ctg aat ggc aag gag tac aag tgc aag gtc tcc aac aaa gcc ctc     1350
Trp Leu Asn Gly Lys Glu Tyr Lys Cys Lys Val Ser Asn Lys Ala Leu
    425                 430                 435 cca gcc ccc atc gag aaa acc atc tcc aaa gcc aaa ggg cag ccc cga     1398
Pro Ala Pro Ile Glu Lys Thr Ile Ser Lys Ala Lys Gly Gln Pro Arg
440                 445                 450                 455 gaa cca cag gtg tac acc ctg ccc cca tcc cgg gat gag ctg acc aag     1446
Glu Pro Gln Val Tyr Thr Leu Pro Pro Ser Arg Asp Glu Leu Thr Lys
                460                 465                 470 aac cag gtc agc ctg acc tgc ctg gtc aaa ggc ttc tat ccc agc gac     1494
Asn Gln Val Ser Leu Thr Cys Leu Val Lys Gly Phe Tyr Pro Ser Asp
            475                 480                 485 atc gcc gtg gag tgg gag agc aat ggg cag ccg gag aac aac tac aag     1542
Ile Ala Val Glu Trp Glu Ser Asn Gly Gln Pro Glu Asn Asn Tyr Lys
        490                 495                 500 acc acg cct ccc gtg ctg gac tcc gac ggc tcc ttc ttc ctc tac agc     1590
Thr Thr Pro Pro Val Leu Asp Ser Asp Gly Ser Phe Phe Leu Tyr Ser
    505                 510                 515 aag ctc acc gtg gac aag agc agg tgg cag cag ggg aac gtc ttc tca     1638
Lys Leu Thr Val Asp Lys Ser Arg Trp Gln Gln Gly Asn Val Phe Ser
520                 525                 530                 535 tgc tcc gtg atg cat gag gct ctg cac aac cac tac acg cag aag agc     1686
Cys Ser Val Met His Glu Ala Leu His Asn His Tyr Thr Gln Lys Ser
                540                 545                 550 ctc tcc ctg tct ccg ggt aaa tgacgcg                                  1714
Leu Ser Leu Ser Pro Gly Lys
            555
```

<210> SEQ ID NO 31
<211> LENGTH: 558
<212> TYPE: PRT
<213> ORGANISM: Homo sapiens

<400> SEQUENCE: 31

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Ala Ser Thr Lys Gly Pro Ser Val Phe Pro Leu Ala
225                 230                 235                 240

Pro Ser Ser Lys Ser Thr Ser Gly Gly Thr Ala Ala Leu Gly Cys Leu
                245                 250                 255

Val Lys Asp Tyr Phe Pro Glu Pro Val Thr Val Ser Trp Asn Ser Gly
            260                 265                 270

Ala Leu Thr Ser Gly Val His Thr Phe Pro Ala Val Leu Gln Ser Ser
        275                 280                 285

Gly Leu Tyr Ser Leu Ser Ser Val Val Thr Val Pro Ser Ser Ser Leu
    290                 295                 300

Gly Thr Gln Thr Tyr Ile Cys Asn Val Asn His Lys Pro Ser Asn Thr
305                 310                 315                 320

Lys Val Asp Lys Lys Val Glu Pro Lys Ser Cys Asp Lys Thr His Thr
                325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
        355                 360                 365

Glu Val Thr Cys Val Val Val Asp Val Ser His Glu Asp Pro Glu Val
    370                 375                 380

```
Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
    450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
        515                 520                 525

Gln Gln Gly Asn Val Phe Ser Cys Ser Val Met His Glu Ala Leu His
    530                 535                 540

Asn His Tyr Thr Gln Lys Ser Leu Ser Leu Ser Pro Gly Lys
545                 550                 555

<210> SEQ ID NO 32
<211> LENGTH: 541
<212> TYPE: PRT
<213> ORGANISM: Homo sapiens

<400> SEQUENCE: 32

Pro Glu Asp Pro Ser Asp Leu Leu Gln His Val Lys Phe Gln Ser Ser
1               5                   10                  15

Asn Phe Glu Asn Ile Leu Thr Trp Asp Ser Gly Pro Glu Gly Thr Pro
                20                  25                  30

Asp Thr Val Tyr Ser Ile Glu Tyr Lys Thr Tyr Gly Glu Arg Asp Trp
            35                  40                  45

Val Ala Lys Lys Gly Cys Gln Arg Ile Thr Arg Lys Ser Cys Asn Leu
        50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met Thr Asp Arg Phe
                85                  90                  95

Ser Ser Leu Gln His Thr Thr Leu Lys Pro Pro Asp Val Thr Cys Ile
            100                 105                 110

Ser Lys Val Arg Ser Ile Gln Met Ile Val His Pro Thr Pro Thr Pro
        115                 120                 125

Ile Arg Ala Gly Asp Gly His Arg Leu Thr Leu Glu Asp Ile Phe His
130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175

Asp Thr Glu Phe Leu Gly Thr Ile Met Ile Cys Val Pro Thr Trp Ala
            180                 185                 190

Lys Glu Ser Ala Pro Tyr Met Cys Arg Val Lys Thr Leu Pro Asp Arg
```

-continued

```
                195                 200                 205
Thr Trp Thr Ala Ser Thr Lys Gly Pro Ser Val Phe Pro Leu Ala Pro
    210                 215                 220

Ser Ser Lys Ser Thr Ser Gly Gly Thr Ala Ala Leu Gly Cys Leu Val
225                 230                 235                 240

Lys Asp Tyr Phe Pro Glu Pro Val Thr Val Ser Trp Asn Ser Gly Ala
                245                 250                 255

Leu Thr Ser Gly Val His Thr Phe Pro Ala Val Leu Gln Ser Ser Gly
            260                 265                 270

Leu Tyr Ser Leu Ser Ser Val Val Thr Val Pro Ser Ser Ser Leu Gly
        275                 280                 285

Thr Gln Thr Tyr Ile Cys Asn Val Asn His Lys Pro Ser Asn Thr Lys
    290                 295                 300

Val Asp Lys Lys Val Glu Pro Lys Ser Cys Asp Lys Thr His Thr Cys
305                 310                 315                 320

Pro Pro Cys Pro Ala Pro Glu Leu Leu Gly Gly Pro Ser Val Phe Leu
                325                 330                 335

Phe Pro Pro Lys Pro Lys Asp Thr Leu Met Ile Ser Arg Thr Pro Glu
            340                 345                 350

Val Thr Cys Val Val Val Asp Val Ser His Glu Asp Pro Glu Val Lys
        355                 360                 365

Phe Asn Trp Tyr Val Asp Gly Val Glu Val His Asn Ala Lys Thr Lys
    370                 375                 380

Pro Arg Glu Glu Gln Tyr Asn Ser Thr Tyr Arg Val Val Ser Val Leu
385                 390                 395                 400

Thr Val Leu His Gln Asp Trp Leu Asn Gly Lys Glu Tyr Lys Cys Lys
                405                 410                 415

Val Ser Asn Lys Ala Leu Pro Ala Pro Ile Glu Lys Thr Ile Ser Lys
            420                 425                 430

Ala Lys Gly Gln Pro Arg Glu Pro Gln Val Tyr Thr Leu Pro Pro Ser
        435                 440                 445

Arg Asp Glu Leu Thr Lys Asn Gln Val Ser Leu Thr Cys Leu Val Lys
    450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
                485                 490                 495

Ser Phe Phe Leu Tyr Ser Lys Leu Thr Val Asp Lys Ser Arg Trp Gln
            500                 505                 510

Gln Gly Asn Val Phe Ser Cys Ser Val Met His Glu Ala Leu His Asn
        515                 520                 525

His Tyr Thr Gln Lys Ser Leu Ser Leu Ser Pro Gly Lys
    530                 535                 540

<210> SEQ ID NO 33
<211> LENGTH: 1011
<212> TYPE: DNA
<213> ORGANISM: Homo sapiens
<220> FEATURE:
<221> NAME/KEY: CDS
<222> LOCATION: (1)...(1008)

<400> SEQUENCE: 33 atg cag act ttc aca atg gtt cta gaa gaa atc tgg aca agt ctt ttc      48
Met Gln Thr Phe Thr Met Val Leu Glu Glu Ile Trp Thr Ser Leu Phe
 1               5                  10                  15
```

-continued

```
atg tgg ttt ttc tac gca ttg att cca tgt ttg ctc aca gat gaa gtg     96
Met Trp Phe Phe Tyr Ala Leu Ile Pro Cys Leu Leu Thr Asp Glu Val
         20                  25                  30 gcc att ctg cct gcc cct cag aac ctc tct gta ctc tca acc aac atg    144
Ala Ile Leu Pro Ala Pro Gln Asn Leu Ser Val Leu Ser Thr Asn Met
     35                  40                  45 aag cat ctc ttg atg tgg agc cca gtg atc gcg cct gga gaa aca gtg    192
Lys His Leu Leu Met Trp Ser Pro Val Ile Ala Pro Gly Glu Thr Val
 50                  55                  60 tac tat tct gtc gaa tac cag ggg gag tac gag agc ctg tac acg agc    240
Tyr Tyr Ser Val Glu Tyr Gln Gly Glu Tyr Glu Ser Leu Tyr Thr Ser
 65                  70                  75                  80 cac atc tgg atc ccc agc agc tgg tgc tca ctc act gaa ggt cct gag    288
His Ile Trp Ile Pro Ser Ser Trp Cys Ser Leu Thr Glu Gly Pro Glu
                 85                  90                  95 tgt gat gtc act gat gac atc acg gcc act gtg cca tac aac ctt cgt    336
Cys Asp Val Thr Asp Asp Ile Thr Ala Thr Val Pro Tyr Asn Leu Arg
            100                 105                 110 gtc agg gcc aca ttg ggc tca cag acc tca gcc tgg agc atc ctg aag    384
Val Arg Ala Thr Leu Gly Ser Gln Thr Ser Ala Trp Ser Ile Leu Lys
        115                 120                 125 cat ccc ttt aat aga aac tca acc atc ctt acc cga cct ggg atg gag    432
His Pro Phe Asn Arg Asn Ser Thr Ile Leu Thr Arg Pro Gly Met Glu
    130                 135                 140 atc acc aaa gat ggc ttc cac ctg gtt att gag ctg gag gac ctg ggg    480
Ile Thr Lys Asp Gly Phe His Leu Val Ile Glu Leu Glu Asp Leu Gly
145                 150                 155                 160 ccc cag ttt gag ttc ctt gtg gcc tac tgg agg agg gag cct ggt gcc    528
Pro Gln Phe Glu Phe Leu Val Ala Tyr Trp Arg Arg Glu Pro Gly Ala
                165                 170                 175 gag gaa cat gtc aaa atg gtg agg agt ggg ggt att cca gtg cac cta    576
Glu Glu His Val Lys Met Val Arg Ser Gly Gly Ile Pro Val His Leu
            180                 185                 190 gaa acc atg gag cca ggg gct gca tac tgt gtg aag gcc cag aca ttc    624
Glu Thr Met Glu Pro Gly Ala Ala Tyr Cys Val Lys Ala Gln Thr Phe
        195                 200                 205 gtg aag gcc att ggg agg tac agc gcc ttc agc cag aca gaa tgt gtg    672
Val Lys Ala Ile Gly Arg Tyr Ser Ala Phe Ser Gln Thr Glu Cys Val
    210                 215                 220 gag gtg caa gga gag gcc act gtg gct gca cca tct gtc ttc atc ttc    720
Glu Val Gln Gly Glu Ala Thr Val Ala Ala Pro Ser Val Phe Ile Phe
225                 230                 235                 240 ccg cca tct gat gag cag ttg aaa tct ggt acc gcc tct gtt gtg tgc    768
Pro Pro Ser Asp Glu Gln Leu Lys Ser Gly Thr Ala Ser Val Val Cys
                245                 250                 255 ctg ctg aat aac ttc tat ccc aga gag gcc aaa gta cag tgg aag gtg    816
Leu Leu Asn Asn Phe Tyr Pro Arg Glu Ala Lys Val Gln Trp Lys Val
            260                 265                 270 gat aac gcc ctc caa tcg ggt aac tcc cag gag agt gtc aca gag cag    864
Asp Asn Ala Leu Gln Ser Gly Asn Ser Gln Glu Ser Val Thr Glu Gln
        275                 280                 285 gac agc aag gac agc acc tac agc ctc agc agc acc ctg acg ctg agc    912
Asp Ser Lys Asp Ser Thr Tyr Ser Leu Ser Ser Thr Leu Thr Leu Ser
    290                 295                 300 aaa gca gac tac gag aaa cac aaa gtc tac gcc tgc gaa gtc acc cat    960
Lys Ala Asp Tyr Glu Lys His Lys Val Tyr Ala Cys Glu Val Thr His
305                 310                 315                 320 cag ggc ctg agc tcg ccc gtc aca aag agc ttc aac agg gga gag tgt   1008
Gln Gly Leu Ser Ser Pro Val Thr Lys Ser Phe Asn Arg Gly Glu Cys
```

-continued 325           330           335
tag                                                      1011

<210> SEQ ID NO 34
<211> LENGTH: 336
<212> TYPE: PRT
<213> ORGANISM: Homo sapiens

<400> SEQUENCE: 34

Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                 85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

<210> SEQ ID NO 35
<211> LENGTH: 307
<212> TYPE: PRT

<213> ORGANISM: Homo sapiens

<400> SEQUENCE: 35

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Thr Val Ala Ala Pro Ser Val
        195                 200                 205

Phe Ile Phe Pro Pro Ser Asp Glu Gln Leu Lys Ser Gly Thr Ala Ser
    210                 215                 220

Val Val Cys Leu Leu Asn Asn Phe Tyr Pro Arg Glu Ala Lys Val Gln
225                 230                 235                 240

Trp Lys Val Asp Asn Ala Leu Gln Ser Gly Asn Ser Gln Glu Ser Val
                245                 250                 255

Thr Glu Gln Asp Ser Lys Asp Ser Thr Tyr Ser Leu Ser Ser Thr Leu
            260                 265                 270

Thr Leu Ser Lys Ala Asp Tyr Glu Lys His Lys Val Tyr Ala Cys Glu
        275                 280                 285

Val Thr His Gln Gly Leu Ser Ser Pro Val Thr Lys Ser Phe Asn Arg
    290                 295                 300

Gly Glu Cys
305

<210> SEQ ID NO 36
<211> LENGTH: 15
<212> TYPE: PRT
<213> ORGANISM: Homo sapiens

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 32
<212> TYPE: DNA

```
<213> ORGANISM: Homo sapiens

<400> SEQUENCE: 37
cgctcgagcc ttccgcaaac ctatgagatc ca                              32

<210> SEQ ID NO 38
<211> LENGTH: 33
<212> TYPE: DNA
<213> ORGANISM: Homo sapiens

<400> SEQUENCE: 38
gcgaattcga gtctaccaaa tgcagacttt cac                             33

<210> SEQ ID NO 39
<211> LENGTH: 18
<212> TYPE: DNA
<213> ORGANISM: Mouse

<400> SEQUENCE: 39
cgccgcgttc ccgagatg                                              18

<210> SEQ ID NO 40
<211> LENGTH: 24
<212> TYPE: DNA
<213> ORGANISM: mouse

<400> SEQUENCE: 40
ggatgaggca gggctgacaa agtt                                       24
```